(12) United States Patent
Hong et al.

(10) Patent No.: US 9,505,763 B2
(45) Date of Patent: Nov. 29, 2016

(54) CANCER TREATMENT USING BMP INHIBITOR

(75) Inventors: Charles C. Hong, Nolensville, TN (US); John Langenfeld, Flemington, NJ (US)

(73) Assignees: Vanderbilt University, Nashville, TN (US); Rutgers, The State University of new Jersey, New Brunswick, NJ (US)

( * ) Notice: Subject to any disclaimer, the term of this patent is extended or adjusted under 35 U.S.C. 154(b) by 14 days.

(21) Appl. No.: 14/234,616

(22) PCT Filed: Jul. 25, 2012

(86) PCT No.: PCT/US2012/048189
§ 371 (c)(1),
(2), (4) Date: May 21, 2014

(87) PCT Pub. No.: WO2013/016452
PCT Pub. Date: Jan. 31, 2013

(65) Prior Publication Data
US 2014/0256720 A1    Sep. 11, 2014

Related U.S. Application Data

(60) Provisional application No. 61/511,188, filed on Jul. 25, 2011.

(51) Int. Cl.
| | | |
|---|---|---|
| A61K 31/519 | (2006.01) |
| C07D 487/04 | (2006.01) |
| A61K 31/5377 | (2006.01) |
| A61N 5/10 | (2006.01) |

(52) U.S. Cl.
CPC ........... *C07D 487/04* (2013.01); *A61K 31/519* (2013.01); *A61K 31/5377* (2013.01); *A61N 5/10* (2013.01)

(58) Field of Classification Search
CPC .................................................. A61K 31/519
USPC ..................................................... 514/259.3
See application file for complete search history.

(56) References Cited

U.S. PATENT DOCUMENTS 8,507,501 B2 * 8/2013 Yu et al. ............... 514/259.3
8,822,684 B1 * 9/2014 Hong et al. ................ 544/281
9,040,694 B1 * 5/2015 Hong et al. ................ 544/281
9,045,484 B2   6/2015 Yu et al.
2010/0093760 A1   4/2010 Yu et al.

FOREIGN PATENT DOCUMENTS

| WO | 2008033408 | 3/2008 |
| WO | WO 2008033408 A2 * | 3/2008 |
| WO | 2009114180 A1 | 9/2009 |
| WO | 2011008640 | 1/2011 |

OTHER PUBLICATIONS

Windholz et al., The Merck Index, 10th Edition, p. 329, abstract No. 2289 (1983).*
Langenfeld EM, Bojnowski J, Perone J, Langenfeld J (2005) Expression of bone morphogenetic proteins in human lung carcinomas. Ann Thorac Surg 80: 1028-1032.
Langenfeld EM, Kong Y, Langenfeld J (2006) Bone morphogenetic protein 2 stimulation of tumor growth involves the activation of Smad-1/5. Oncogene 25: 685-692.
Hao, J., et al.; In Vivo Structure—Activity Relationship Study of Dorsomorphin Analogues Identifies Selective VEGF and BMP Inhibitors; ACS Chemical Biology; vol. 5; No. 2; 2009; pp. 245-253.
Alarmo, et al., Bone Morphogenetic Protein 7 Is Widely Overexpressed in Primary Breast Cancer; Genes, Chromosomes & Cancer, 2006, 45:411-419.
Kim, et al., Expression of Bone Morphogenetic Protein Receptors Type-IA, -IB, and -II Correlates with Tumor Grade in Human Prostate Cancer Tissues, Cancer Research Jun. 1, 2000, 60, 2840-2844.
Kim, et al., Decreased Expression of Bone Morphogenetic Protein (BMP) Receptor Type II Correlates with Insensitivity to BMP-6 in Human Renal Cell Carcinoma Cells, Clinical Cancer Research, Dec. 1, 2003, vol. 9, 6046-6051.
Kim, et a., Loss of expression of bone morphogenetic protein receptor type II in human prostate cancer cells, Oncogene (2004) 23, 7651-7659.
Waite, et al., From Developmental Disorder to Heritable Cancer: It's All in the BMP/TGF-βFamily, Nature, Oct. 2003, vol. 4, pp. 763-773.

* cited by examiner

*Primary Examiner* — Kevin E Weddington
(74) *Attorney, Agent, or Firm* — Stites & Harbison PLLC; Mandy Wilson Decker

(57) ABSTRACT

Methods for regulating cancer cell growth and survival, inhibiting cancer cell growth, promoting cancer cell death, and/or treating a cancer make use of antagonists of a type I BMP receptor. In some embodiments the cancer is a lung cancer and the cancer cell is a lung cancer cell.

14 Claims, 10 Drawing Sheets

H1299 Cells

CANCER TREATMENT USING BMP INHIBITOR

RELATED APPLICATION

This application claims priority from U.S. Provisional Application Ser. No. 61/511,188 filed Jul. 25, 2011, the entire disclosure of which is incorporated herein by this reference.

TECHNICAL FIELD

The presently-disclosed subject matter relates to cancer therapeutics. In particular, the presently-disclosed subject matter relates to inhibiting lung cancer cell growth and promoting lung cancer cell death.

INTRODUCTION

Bone morphogenetic proteins (BMPs) are among a family of signaling molecules —the transforming growth factor beta (TGFβ) molecules. They are involved in the development and maturation of tissues during various biological processes including differentiation, proliferation, apoptosis and epithelial-mesenchymal transition (EMT). Although, the BMP signaling pathway has been shown to be active in many different types of cancers, there is no conclusive evidence that it promotes cell growth and/or survival in cancer. Inhibition of this signaling pathway has been difficult because of a redundant family of proteins and receptors that activate the signaling cascade.

BMP signaling is also essential for multiple aspects of development, which includes the regulation of cell fate decisions, cell survival, and vasculogenesis. BMP-2 is frequently over-expressed in lung and other carcinomas. Studies have shown that BMP-2 enhances tumor angiogenesis and stimulates tumor invasion. Ectopic expression of BMP-2 in A549 cells has been shown to greatly enhance metastatic growth in the lungs of mice following tail vein injection. The precise effects of BMP signaling on cell growth and survival of cancer cells are poorly understood. Studies using recombinant BMP proteins or knockdown of a single BMP receptor have suggested that the BMP signaling cascade inhibits the growth of cancer cells. The complex and redundant BMP signaling cascade would suggest that inhibition of multiple BMP receptors is required to abrogate the BMP signaling in cancer cells.

The inhibitor of DNA binding/differentiation (Id) is a family of helix-loop-helix (HLH) transcriptional regulatory proteins. There are 4 Id family members (Id1, Id2, Id3, and Id4). The Id proteins inhibit lineage commitment of multiple cell types by binding and sequestering basic HLH transcription factors. Id family members have been implicated in oncogenic transformation in several types of cancers. Id1 regulates invasion, proliferation, cell survival, tumor angiogenesis, and metastatic growth. A higher expression of Id1 in adenocarcinomas of the lung was associated with a shorter disease-free survival regardless of stage. Over-expression of Id1 immortalizes primary keratinocytes. Id1 null mouse embryo fibroblasts and knockdown of Id1 in human fibroblasts induces cellular senescence. Furthermore, mice over-expressing Id1 and RAS in breast epithelium develop metastatic breast cancer. Id1 is thought to promote transformation by blocking Ras induced senescence. Inactivation of Id1 in established breast tumors led to senescence, growth arrest, and tumor regression. Forced expression of Id1 in the intestine leads to adenocarcinomas in mice.

The BMPs signaling occurs through type I (alk2, alk3, and alk6) and type II (ActR-II, Acr-IIB, and BMPR-II) receptors. Activation of the BMP receptors by the ligands phosphorylates Smad 1/5 and 8, which then translocate to the nucleus, activating downstream targets. Known direct targets of BMP in stem cells are Id1, Id2, and Id3. Id1-3 has been shown to regulate many important functions in cancer cells including enhancing cell migration, metastasis, proliferation. Id1 also inhibits senescence and apoptosis. Id1 may be regulated by other oncogenes in cancer including c-Myc and Src. Although BMP has been shown to induce transient increase in Id1 in cancer cells, its role in regulating the basal expression levels of Id1-3 in cancer has not been shown.

Expression of Id family members in cancer is mediated by activated RAS, MYC, and TP53 gain of function. As noted above, Src has recently been shown to regulate Id1 expression, which is mediated through the BMP signaling cascade. BMP response elements (BRE) on the Id1, Id2, and Id3 promoters are activated by Smad 1/5/8. Recombinant BMP-2 protein transiently activates Smad 1/5/8 and Id1 in the A549 and H1299 lung cancer cell lines, indicating an intact signaling mechanism. The role of basally active BMP signaling in regulating the expression of Id family members in cancer cells has not been elucidated.

To date, there has been no conclusive data that the BMP signaling cascade has any significant effect on the growth or survival of cancer cells. Prior studies have shown that BMPs produce only a transient increase in cell proliferation or none at all. Several studies have suggested that activation of the BMP signaling cascade decreases the growth of cancer cells. The positive growth effects of BMP in cancer have been attributed to its effects on angiogenesis. Thus, there remains a need for a clear demonstration of the connection between the BMP signaling pathway and cancer cell growth, as well as new therapeutic agents which make use of this relationship to regulate cancer cell survival.

SUMMARY

The presently-disclosed subject matter meets some or all of the above-identified needs, as will become evident to those of ordinary skill in the art after a study of information provided in this document.

In some embodiments of the presently-disclosed subject matter a method is provided for inhibiting cancer cell growth, promoting cancer cell death, and/or treating cancer comprising using an identified class of small molecule antagonists to inhibit the function of BMP receptors found on cancer cells, thus promoting cell death. BMPs are aberrantly expressed in many carcinomas but their effects on self-autonomous cell growth and survival are poorly understood. As disclosed herein, BMP Smad 1/5/8 transcription factors are basally active in lung cancer cell lines, which can be effectively inhibited with selective antagonists of the type I BMP receptors. Blockade of the type I BMP receptors induces a significant decrease in the expression of inhibitor of differentiation (Id1, Id2, and Id3) family members, which are known to regulate cell growth and survival in many types of cancer cells. Inhibition of all type I BMP receptors (alk2, alk3, and alk6) caused the most effective reduction in BMP signaling in lung cancer cell lines. BMP receptor antagonists decreased cell growth and clonigenicity with the greatest reduction occurring with the antagonists that most effectively blocked all type I receptors. BMP receptor antagonists and silencing of all type I BMP receptors with RNAi induced cell death. Forced expression of only Id1 does not over-come the growth suppressive effects of the BMP antagonists, suggesting that BMPs may signal through more than one Id family member. These studies show that self-autonomous activation of the BMP signaling cascade regulates expression of Id family members and promotes cell growth and survival of lung cancer cells. As disclosed herein, selective antagonists of the type I BMP receptors can be used to pharmacologically treat cancers with an activated BMP signaling cascade.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

Figure 9:
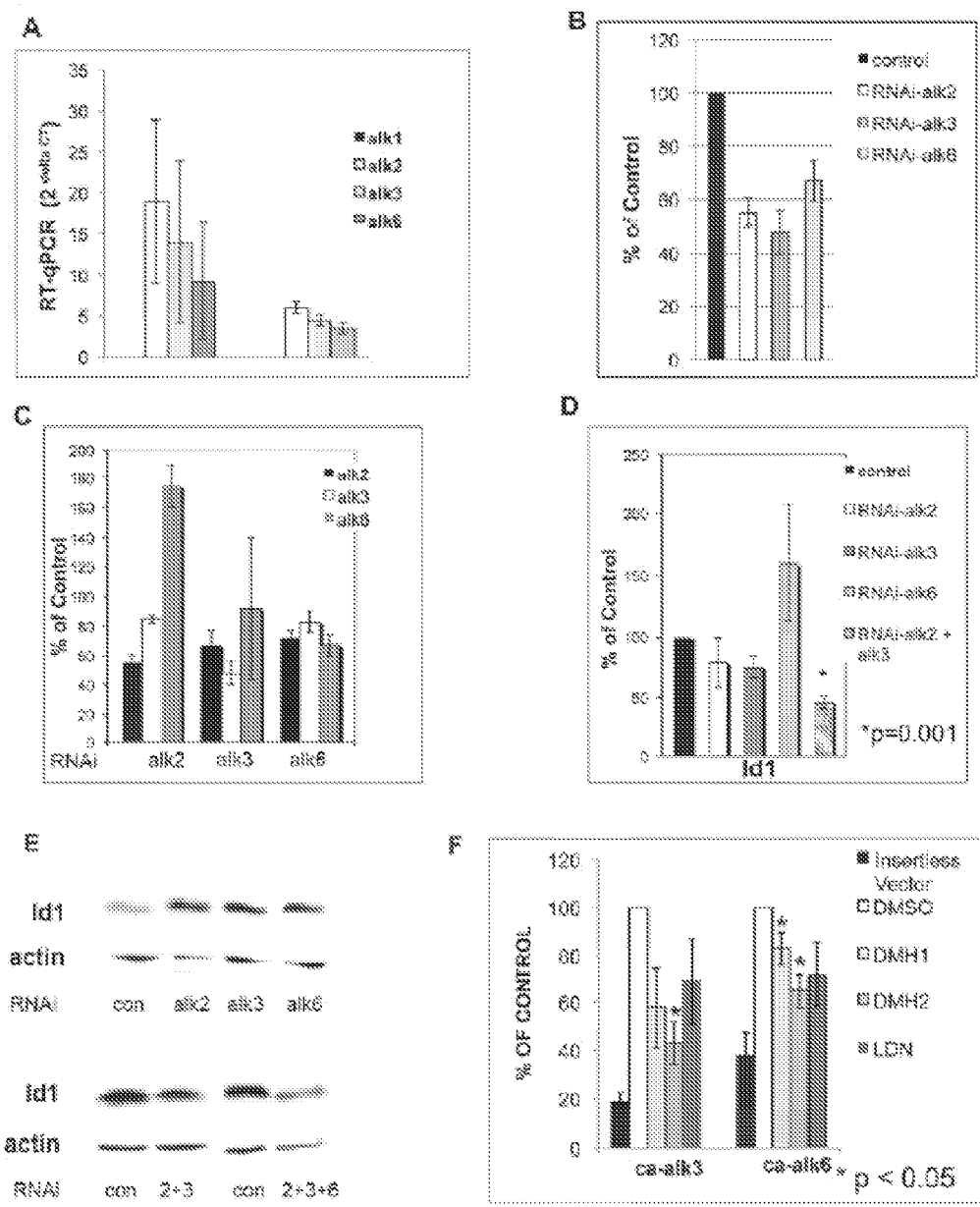

FIG. 9 Multiple BMP type I receptors mediate BMP signaling in lung cancer cell lines. (A) Quantitative RT-PCR of the A549 and H1299 cells showing expression of alk2, alk3, and alk6 but not alk1 (n=3). (B) H1299 cells were transfected with siRNA targeting each type I BMP receptor and quantitative RT-PCR was performed for that BMP receptor. (C) Knockdown of each BMP type I receptor in H1299 cells was performed and quantitative RT-PCR performed for all 3 type I receptors. (B-C) Data represents the mean of 2 experiments performed in duplicate. (D) Knockdown in H1299 cells of a single BMP type I receptor or both alk2 and alk3. After 48 hours the expression of Id1 was examined by quantitative RT-PCR. Data represents the mean of 3 experiments performed in duplicate. (E) Western blot analysis for Id1 in H1299 cells with knockdown of a single type I BMP receptor or combination knockdown of alk2 and alk3, or all 3 BMP type I receptors. Studies were done at least 2 times. Studies show silencing more than one receptor is required to decrease Id1 expression. (F) H1299 cells were co-transfected with insertless vector, constitutively active alk3 (ca-alk3), or constitutively active alk6 (ca-alk6) expression vectors and the BRE-luciferase reporter. Cells were then treated with 1 μM DMSO or 1 μM BMP receptor antagonist for 24 hours and luciferace activity measured. Data demonstrates the mean of at least 3 independent shown as the percent of control.

Figure 10:
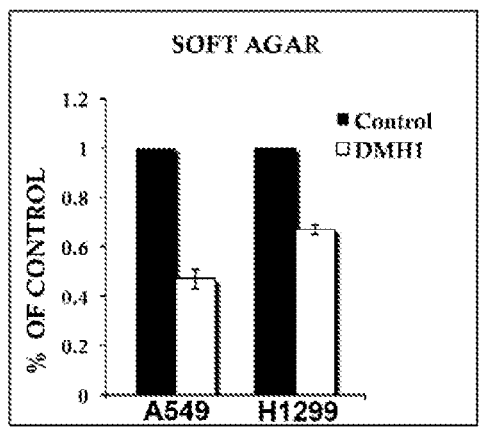

FIG. 10 demonstrates the antagonizing BMP signaling decreases anchorage independent growth of lung cancer cells. A549 cells in soft agar were treated with DMSO or DMH1 for 2 weeks and the number of colonies counted. The data is reported as the mean of 3 independent experiments.

Figure 11:
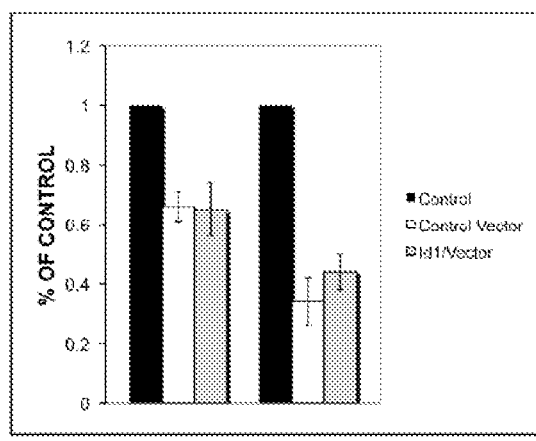

FIG. 11 shows the forced expression of Id1 does not prevent the anti-tumorigenic effects of antagonizing BMP signaling. (A) Id1 expression vector and control vector were stably expressed in the H1299 cells. Western blot analysis showing over-expression of Id1. (B) The H1299/Id1 and control cells were treated for 7 days and cell counts performed. (C) Clonal growth assays of H1299/Id1 and control cells treated with DMH2 for 2 weeks.

Figure 12:
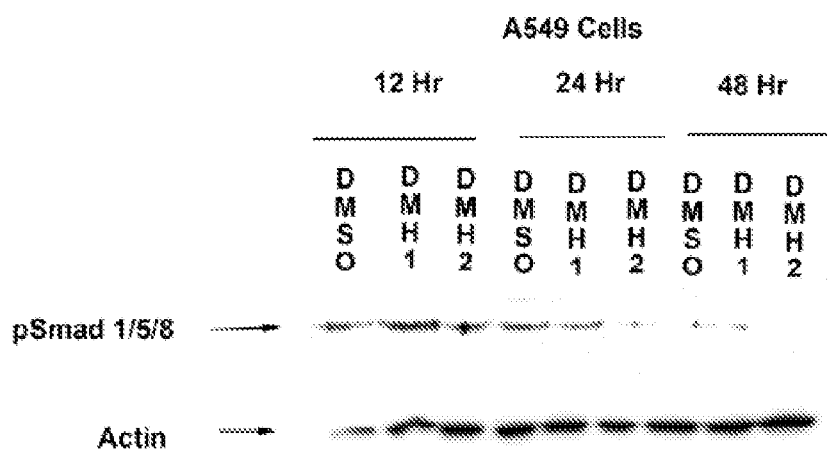

FIG. 12 shows that DMH2 decreases phosphorylated Smad 1/5/8 expression in A549 cells. Western blot analysis for pSmad 1/5/8 on A549 cells treated with 1 μM DMSO, DMH1 or DMH2 for 12, 24, and 24 hours.

Figure 13:
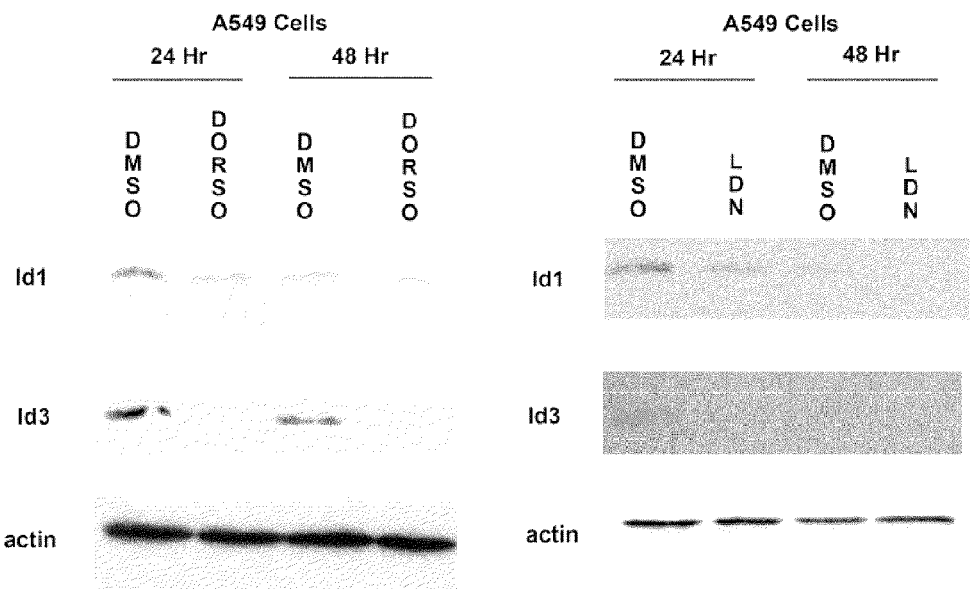

FIG. 13 shows that Dorsomorphin and LDN decrease protein expression of Id1 and Id3. Western blot analysis for Id1 and Id3 on A549 cells treated with 10 μM Dorsomorphin or 1 μM LDN for 24 and 48 hours.

Figure 14:
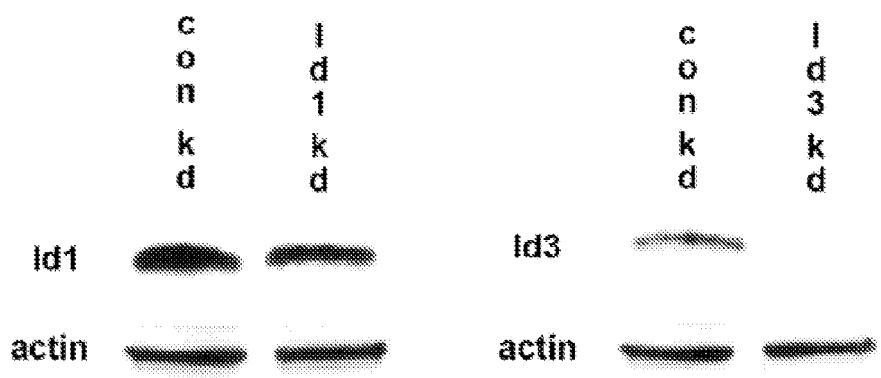

FIG. 14 shows Western blot analysis of H1299 cells transfected with siRNA targeting Id1 or Id3. H1299 cells were transfected with control siRNA and siRNA targeting Id1 or Id3. After 48 hours Western blot analysis was performed using monoclonal antibodies detecting Id1 or Id3.

Figure 15:
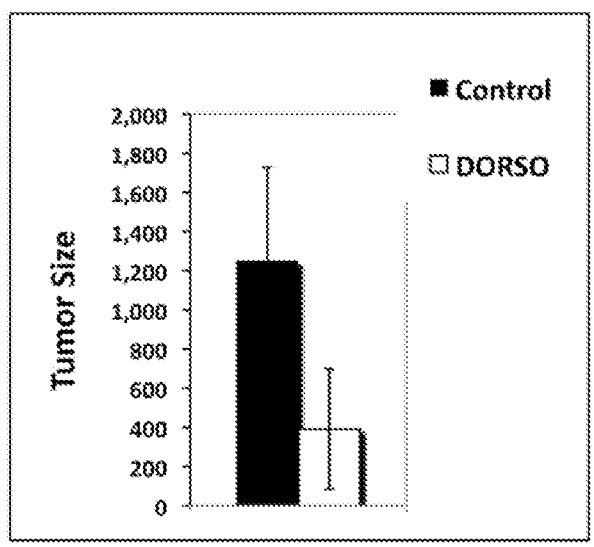

FIG. 15 shows that tumor size is reduced in response to treatment with a BMP inhibitor. H1299 tumors approximately 100 mm$^3$ in size were injected around the tumor with DMSO or Dorsomorphin (40 μM) 3 times weekly. Tumor size was determined 3 weeks after initiation of treatment. (n=6)

DESCRIPTION OF EXEMPLARY EMBODIMENTS

The presently-disclosed subject matter includes methods and kits useful for regulating cancer cell growth and survival, inhibiting cancer cell growth, promoting cancer cell death, and/or treating a cancer. In some embodiments the cancer is a lung cancer and the cancer cell is a lung cancer cell.

Methods and kits of the presently-disclosed subject matter make use of antagonists of a type I BMP receptor. In some embodiments, the antagonist is a small molecule, as opposed to a polypeptide. Antagonists of a type I BMP receptor are also referred to herein BMP inhibitors, because they can specifically block or inhibit the BMP signaling cascade that is active in many cancers.

As used herein, the terms "inhibit", "inhibitor", or "inhibiting" are not meant to require complete inhibition, but refers to a reduction in signaling. Such reduction can be a reduction by at least about 50%, at least about 75%, at least about 90%, or at least about 95% of the signaling in the absence of the inhibitory effect, e.g., in the absence of a compound that is an inhibitor of the signaling.

In some embodiments, the BMP inhibitor is a compound of the formula

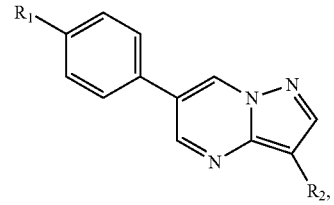

or an analog thereof, wherein $R_1$ is selected from the group consisting of alkyl, branched alkyl, substituted alkyl, aryl, substituted aryl, alkoxy, amino, and dialkylamino; wherein $R_2$ is selected from the group consisting of

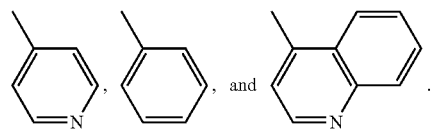

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, methylpropynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes, but is not limited to, alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

The term "alkoxy" is used herein to refer to a —OZ$^1$ radical, where Z$^1$ is selected from the group consisting of alkyl, substituted alkyl, cycloalkyl, substituted cycloalkyl, heterocycloalkyl, substituted heterocycloalkyl, silyl groups, and combinations thereof as described herein. Suitable alkoxy radicals include, for example, methoxy, ethoxy, benzyloxy, t-butoxy, etc. A related term is "aryloxy" where Z$^1$ is selected from the group consisting of aryl, substituted aryl, heteroaryl, substituted heteroaryl, and combinations thereof. Examples of suitable aryloxy radicals include phenoxy, substituted phenoxy, 2-pyridinoxy, 8-quinalinoxy, and the like.

The term "amino" is used herein to refer to the group —NZ$^1$Z$^2$, where each of Z$^1$ and Z$^2$ is independently selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl, and combinations thereof. Additionally, the amino group can be represented as —NZ$^1$Z$^2$ Z$^3$, with the previous definitions applying and Z$^3$ being either H or alkyl.

"Dialkylamino" refers to an —NXX' group wherein each of X and X' is independently an alkyl group as previously described. Exemplary alkylamino groups include ethylmethylamino, dimethylamino, and diethylamino.

When the term "independently selected" is used, the substituents being referred to (e.g., Z$^1$ and Z$^2$), can be identical or different. For example, both Z$^1$ and Z$^2$ can be substituted alkyls, or Z$^1$ can be hydrogen and Z$^2$ can be a substituted alkyl, and the like.

In some embodiments of the presently-disclosed subject matter, R$_1$ is selected from the group consisting of

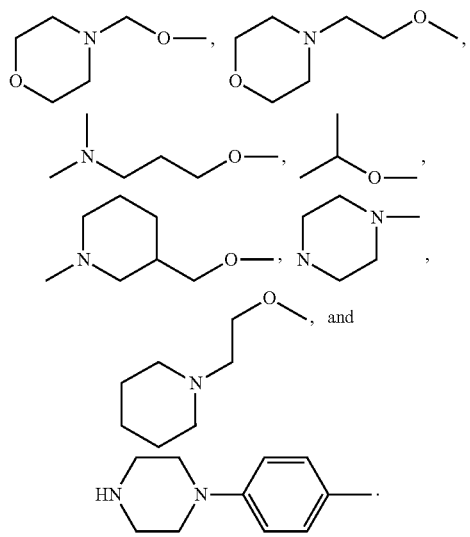

In some embodiments of the presently-disclosed subject matter, R$_2$ is selected from the group consisting of

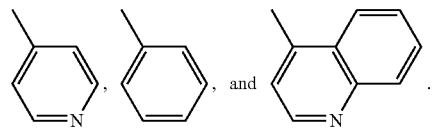

In some embodiments, the BMP inhibitor is a compound of the formula,

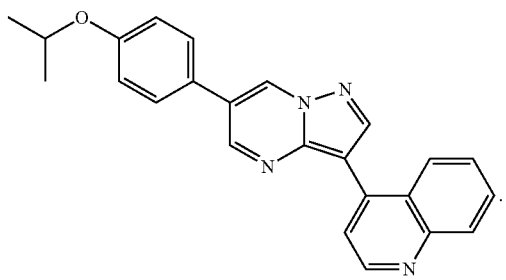 [SMILES: CC(C)Oc1ccc(-c2cnc3c(-c4ccnc5ccccc45)cnn3c2)cc1]

This compound is also referred to herein as DMH1.

In some embodiments, the BMP inhibitor is a compound of the formula,

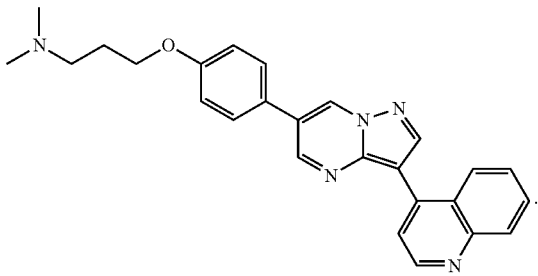 [SMILES: CN(C)CCCOc1ccc(-c2cnc3c(-c4ccnc5ccccc45)cnn3c2)cc1]

This compound is also referred to herein as DMH2.

In some embodiments, the BMP inhibitor is a compound of the formula,

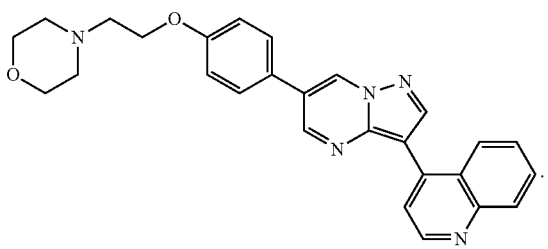 [SMILES: c1ccc2c(-c3cnn4cc(-c5ccc(OCCN6CCOCC6)cc5)cnc34)ccnc2c1]

This compound is also referred to herein as DMH3.

In some embodiments of the presently-disclosed subject matter a method of inhibiting cancer cell growth and/or promoting cancer cell death includes administering to a cancer cell an effective amount of an antagonist of a type I BMP receptor. In some embodiments of the presently-disclosed subject matter a method of treating a cancer in a subject in need thereof includes administering to the subject an effective amount of an antagonist of a type I BMP receptor. In some embodiments of the presently-disclosed subject matter, an antagonist of a type I BMP receptor is administered to selectively target a cancer cell.

As used herein, the term "effective amount" refers to a dosage sufficient to provide treating a desired effect, such as inhibition of cancer cell growth, promotion of cancer cell death, and/or treatment of a cancer. As will be recognized by those of ordinary skill in the art, this amount can vary depending on the cell or cells, the subject, the particular cancer, severity of the cancer, and/or the particular goals of the therapy. The exact amount that is required will vary from cell(s) to cell(s) and from subject to subject, depending on the species, age, and general condition, the particular carrier or adjuvant being used, mode of administration, and the like. As such, the effective amount will vary based on the particular circumstances, and an appropriate effective amount can be determined in a particular case by one of ordinary skill in the art using only routine experimentation.

As used herein, the terms "treatment" or "treating" relate to any treatment of a cancer, including but not limited to prophylactic treatment and therapeutic treatment. The terms relate to medical management of a subject with the intent to substantially cure, ameliorate, stabilize, or substantially prevent a cancer from progressing, including but not limited to prophylactic treatment to preclude, avert, obviate, forestall, stop, or hinder something from happening, or reduce the severity of something happening, especially by advance action. As such, the terms treatment or treating include, but are not limited to: inhibiting the progression of a cancer; arresting or preventing the development of a cancer; reducing the severity of a cancer; ameliorating or relieving symptoms associated with a cancer; causing a regression of a cancer or one or more of the symptoms associated with a cancer; and preventing a cancer or the development of a cancer. The terms includes active treatment, that is, treatment directed specifically toward the improvement of a cancer, and also includes causal treatment, that is, treatment directed toward removal of the cause of the cancer. In addition, the terms includes palliative treatment, that is, treatment designed for the relief of symptoms rather than the curing of the cancer; preventative treatment, that is, treatment directed to minimizing or partially or completely inhibiting the development of the associated cancer; and supportive treatment, that is, treatment employed to supplement another specific therapy directed toward the improvement of the associated cancer.

In some embodiments, the BMP inhibitors as described herein can be provided as a pharmaceutically-acceptable salt or solvate. Suitable acids and/suitable bases, as will be known to those of ordinary skill in the art, are capable of forming salts of the compounds described herein, e.g., hydrochloric acid (HCl), sodium hydroxide. In some embodiments, the BMP inhibitors can be provided as a pharmaceutically-acceptable solvate. A solvate is a complex or aggregate formed by one or more molecules of a solute, e.g. a compound or a pharmaceutically-acceptable salt thereof, and one or more molecules of a solvent. Such solvates can be crystalline solids having a substantially fixed molar ratio of solute and solvent. Suitable solvents will be known by those of ordinary skill in the art, e.g., water, ethanol.

The BMP inhibitors as described herein can be provided in a medicament for the treatment of a cancer, such as a lung cancer.

As will be understood by those of ordinary skill in the art, a dosage regimen can be adjusted to provide an optimum treatment effect and can be administered daily, biweekly, weekly, bimonthly, monthly, or at other appropriate time intervals. As will be understood by those of ordinary skill in the art, BMP inhibitors can be administered by methods known to those of ordinary skill in the art based on the circumstances. In some embodiments, direct application to a cell or cells is appropriate. In some embodiments, administration can be orally, intravenously, intramuscularly, subcutaneously, or by other art-recognized means.

For oral administration, the compositions can take the form of, for example, tablets or capsules prepared by a conventional technique with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets can be coated by methods known in the art. Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives such as suspending agents (e.g., sorbitol syrup, cellulose derivatives or hydrogenated edible fats); emulsifying agents (e.g.

lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration the compositions can take the form of tablets or lozenges formulated in conventional manner.

The compounds can also be formulated as a preparation for injection. Thus, for example, the compounds can be formulated with a suitable carrier. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants.

As used herein, the term subject refers to humans and other animals. Thus, veterinary uses are provided in accordance with the presently disclosed subject matter. The presently disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

In some embodiments of the presently-disclosed subject matter, the antagonist of a type I BMP receptor can be administered as part of a treatment plan that further includes use of an anti-cancer agent and/or radiation.

As such, methods of the presently-disclosed subject matter include administering a BMP inhibitor in combination with an anti-cancer agent. As used herein, the term "anti-cancer agent" refers to an agent that is capable of affecting a treatment as defined herein. For example, the anti-cancer agent may kill cancer cells, induce apoptosis in cancer cells, reduce the growth rate of cancer cells, reduce the incidence or number of metastases, reduce tumor size, inhibit tumor growth, reduce the blood supply to a tumor or cancer cells, promote an immune response against cancer cells or a tumor, prevent or inhibit the progression of cancer, or increase the lifespan of a subject with cancer.

Examples of anti-cancer agents include, but are not limited to, platinum coordination compounds such as cisplatin, carboplatin, or oxalyplatin; taxane compounds, such as paclitaxel or docetaxel; topoisomerase I inhibitors, such as camptothecin compounds for example irinotecan or topotecan; topoisomerase II inhibitors, such as anti-tumor podophyllotoxin derivatives for example etoposide or teniposide; anti-tumor vinca alkaloids for example vinblastine, vincristine or vinorelbine; anti-tumor nucleoside derivatives for example 5-fluorouracil, gemcitabine or capecitabine; alkylating agents, such as nitrogen mustard or nitrosourea for example cyclophosphamide, chlorambucil, carmustine or lomustine; anti-tumor anthracycline derivatives for example daunorubicin, doxorubicin, idarubicin or mitoxantrone; HER2 antibodies for example trastuzumab; estrogen receptor antagonists or selective estrogen receptor modulators for example tamoxifen, toremifene, droloxifene, faslodex or raloxifene; aromatase inhibitors, such as exemestane, anastrozole, letrazole and vorozole; differentiating agents, such as retinoids, vitamin D and retinoic acid metabolism blocking agents (RAMBA) for example accutane; DNA methyl transferase inhibitors for example azacytidine; kinase inhibitors for example flavoperidol, imatinib mesylate or gefitinib; farnesyltransferase inhibitors; HDAC inhibitors; other inhibitors of the ubiquitin-proteasome pathway for example Velcade; or Yondelis; or estrogen derivatives, such as estramustine. As will be apparent to those skilled in the art, the particular anti-cancer agent that is selected can vary, depending on the particular cancer being treated.

Methods of the presently-disclosed subject matter include administering a BMP inhibitor in combination with radiation. The term "radiation", as used herein, refers to any radiation that may be used in cancer treatment to control cancer cells. The radiation may be a curative, adjuvant, or palliative radiotherapy. Such radiation includes, but is not limited to, various forms of ionizing radiation, external bean radiotherapy (EBRT or XBRT) or teletherapy, brachytherapy or sealed source therapy, intraoperative radiotherapy, and unsealed source radiotherapy. In some embodiments, the radiation is ionizing radiation.

In some embodiments, the administration of the combination of the BMP inhibitor and the anti-cancer agent and/or the radiation produces an effect that exceeds the effect of either the BMP inhibitor alone or the anti-cancer agent and/or the radiation alone. In some embodiments, the administration of the combination of the BMP inhibitor and the anti-cancer agent and/or the radiation produces a synergistic effect.

As used herein, "synergy" or "synergistic effect" can refer to any substantial enhancement, seen with the administration of a BMP inhibitor in combination with an anti-cancer agent and/or radiation, of a measurable effect, e.g. a cancer cell killing or growth inhibition effect, when compared with the effect of a BMP inhibitor alone or an anti-cancer agent and/or the radiation alone. Synergy is a specific feature of the presently-disclosed subject matter, and is above any background level of enhancement that would be due solely to, for example, additive effects.

In some embodiments, a substantial enhancement of a measurable effect can be expressed as a combination index (CI). CI can be calculated for each combination of a BMP inhibitor and anti-cancer agent using, for example Calcusyn software (Biosoft, Cambridge, United Kingdom), which performs calculations and quantifies synergy using the Median Effect methods described by T-C Chou and P. Talalay (Trends Pharmacol. Sci. 4, 450-454), which is incorporated herein by this reference. In some embodiments, a substantial enhancement of a measurable effect is found when CI, calculated using CalcuSyn Version 2.0, is less than about 0.65, 0.70, 0.75, 0.80 or 0.85.

The term "in combination with", when used herein to describe administering a BMP inhibitor and an anti-cancer agent and/or radiation refers to administering a BMP inhibitor to a subject and administering an anti-cancer agent and/or radiation to the subject. In some embodiments, the BMP inhibitor is administered before the anti-cancer agent and/or the radiation is administered. In some embodiments, the BMP inhibitor is administered after the anti-cancer agent and/or the radiation is administered. In some embodiments, the BMP inhibitor and the anti-cancer agent and/or the radiation are administered concurrently. In some embodiments, a BMP inhibitor and an anti-cancer agent are formulated in a composition for concurrent administration.

Embodiments of the presently-disclosed subject matter further include kits, comprising an antagonist of a type I BMP receptor, as described hereinabove. In embodiments of such kits, an antagonist can be packaged together with a device for use in administration of the antagonist, as will be recognized by those skilled in the art. In some embodiments, a kit can include an anti-cancer agent. In some embodiments, a kit can include instructions directing administration of the antagonist.

The presently-disclosed subject matter further includes a method for use in drug discovery, wherein the methods described herein can be used to experimentally alter the BMP signaling pathway to facilitate comprehensive understanding of specific causes of various conditions, as well as the exploration of potential therapies.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments±20%, in some embodiments±10%, in some embodiments±5%, in some embodiments±1%, in some embodiments±0.5%, and in some embodiments±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is further illustrated by the following specific but non-limiting examples. The following examples may include compilations of data that are representative of data gathered at various times during the course of development and experimentation related to the present invention.

EXAMPLES

Example 1

As disclosed herein, it has been determined that certain small molecule BMP inhibitors can inhibit the function of a specific set of receptors found on cancer cells, thus promoting cell death. These small molecule antagonists specifically block the BMP signaling cascade that is active in many cancers. They further decrease cell growth and induce cell death of cancer cells and provide a direct link between this signaling pathway and the promotion growth and/or survival in cancer cells. Thus the presently-disclosed subject matter provides for a unique method of regulating cancer cell growth and survival, and identifies compositions and compounds useful for treatment of cancer and/or useful for regulating cancer cell growth and survival.

As disclosed herein, bone morphogenetic protein 2 is highly expressed in the majority of lung carcinomas. There are at least 14 other family members, which include BMP-4, BMP6, BMP7, and GFD 5. BMPs are expressed in many other tumors including breast, prostate, colon, esophageal, kidney, osteosarcomas, head and neck, ovarian, liver, brain, and pancreatic carcinomas. BMPs are also expressed in leukemias and germ cell tumors. BMPs have been shown to promote metastasis to bone. However, to date, there has been no conclusive data that the BMP signaling cascade has any significant effect on the growth or survival of cancer cells.

The difficulty in understanding the role of BMP signaling cascade in cancer is the promiscuity of the receptors to the BMP ligands. The discoveries disclosed herein demonstrate that inhibition of the type I BMP receptors in cancer cells decreases clonogenicity, anchorage-independent growth, and induces cell death. This is associated with a significant decrease in the expression of Id1, Id2, and Id3. As also disclosed herein, inhibition of the BMP type I receptors in cancer cells can be achieved with small molecules, which specifically target these receptors. The studies described herein show that inhibition of the BMP signaling cascade with selective small molecule antagonist of the type I BMP receptors will cause a significant reduction in tumor growth from lung and other carcinomas.

DMH1, DMH2, and LDN-193189 are selective type I BMP antagonists, which have been shown, for the first time as part of the present invention, to down-regulate Id1-Id3, decrease colonogenicity, decrease anchorage independent growth, and induce cell death in cancer cells. The most potent selective small molecule BMP antagonist studied thus far is DMH2. The studies reveal that these small molecules or those with same basic structure can be used as potential drugs to treat cancer.

Figure 1:
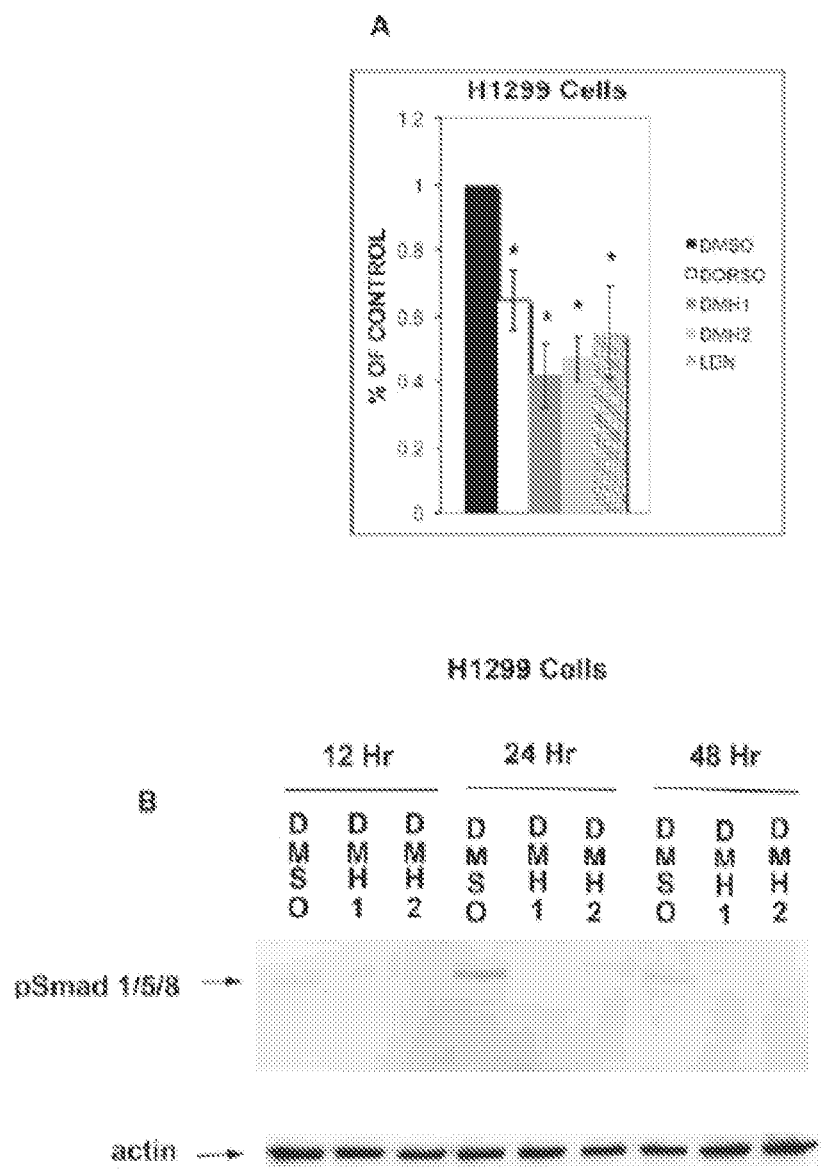
FIG. 1 shows BMP type I receptor antagonist decrease Smad 1/5/8 activity in lung cancer cells. (A) H1299 cells were transfected with BRE-luciferase reporter. After 48 hours the cells were treated with DMSO or BMP receptor antagonists (10 µM Dorsomorphin, or 1 µM DMH1, 1 µM DMH2, or 1 µM LDN) for 48 hours. BRE-luciferase activity is reported as the percent of the DMSO control treated cells. Data represents the mean of 3 experiments performed in triplecate. The mean of the control cells was compared to the mean of the treated cells. * p<0.05. (B) Western blot analysis for phosphorylated Smad 1/5/8 on H1299 cells treated with 1 µM DMSO, DMH1, or DMH2 for 12, 24, and 48 hours.
Figure 6:
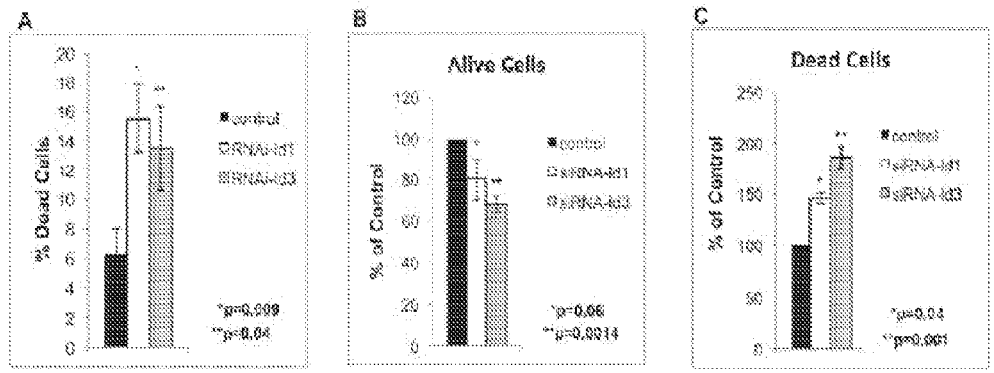
FIG. 6 indicates that Id1 and Id3 regulate cell growth and survival of lung cancer cells. (A) H1299 cells were transfected with control siRNA and siRNA targeting Id1 or Id3. After 2 days the percentage of cells staining for ethidium bromide was determined. The data is reported as the mean of 4 independent experiments. (B-C) H1299 cells were transfected with control siRNA and siRNA targeting Id1 or Id3. After 7 days the cells were stained with Trypan Blue and the percentage of (B) alive and (C) dead cells was determined. The data represents the mean of 3 experiments reported as the percent of control.

The effects of basal BMP signaling in lung cancer cell lines were examined using specific BMP type I receptors antagonists. LDN is a Dorsomorphin analogue that has less activity for AMP kinase than Dorsomorphin. DMH1 and DMH2 are specific Dorsomorphin analogues that have less activity for VEGF II, AMP kinase, TGFβ receptor alk5, and platelet-derived growth factor receptor-β than Dorsomorphin or LDN. BMP-responsive luciferase assays show that Dorsomorphin, DMH1, DMH2, and LDN decrease Smad 1/5/8 activity in lung cancer cell lines (FIG. 1A). By Western blot analysis, Dorsomorphin, DMH1, DMH2, and LDN all decreased the level of phosphorylated Smad 1/5/8 expression in lung cancer cell lines (FIGS. 1B and 6). BMP receptor antagonist decreased Smad 1/5/8 activity within 12 hours and persisted for at least 48 hours. These studies demonstrate that there is basal BMP signaling activity in lung cancer cell lines, which can be inhibited by antagonizing the type I BMP receptors.

Figure 2:
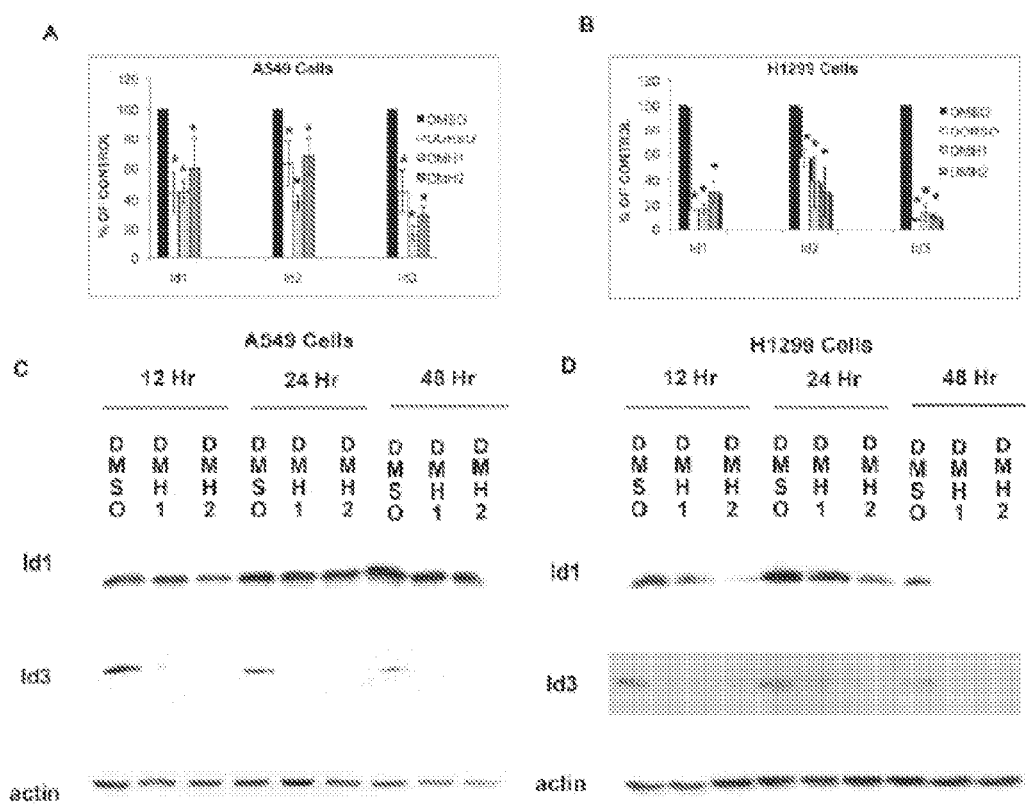
FIG. 2 BMP antagonists decrease the expression of Id family members in A549 and H1299 cells. (A-B) Quantitative RT-PCR for Id1, Id2, and Id3 on (A) A549 and (B) H1299 cells treated with DMSO, 10 µM Dorsomorphin, 1 µM DMH1, or 1 µM DMH2 for 48 hours. Data represents the mean of at least 3 experiments performed in duplicate and presented as the percent of control treated cells. The mean of the control cells was compared to the mean of the treated cells. * p<0.05. (C-D) Western blot analysis for Id1 and Id3 on (C) A549 and (D) H1299 cells treated with 1 µM DMSO or 1 µM of selective BMP type I receptor antagonist for 12, 24, and 48 hours. These studies were performed at least 3 times.
Figure 7A:
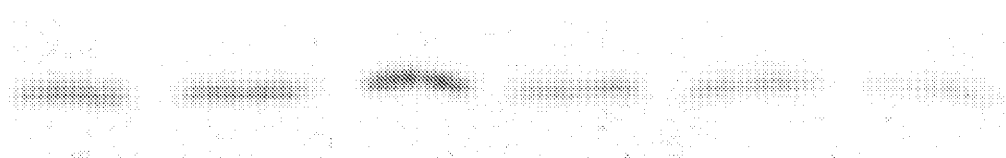
FIG. 7A depicts that Dorsomorphin and LDN decrease the expression of phosphorylated Smad 1/5/8 in lung cancer cells. Western blot analysis for pSmad 1/5/8 on A549 cells treated with Dorsomorphin and LDN.
Figure 7B:
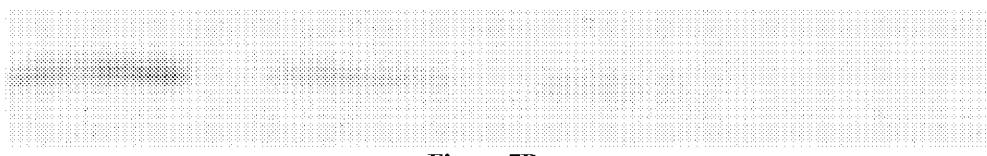
FIG. 7B shows that Dorsomorphin and LDN decrease protein expression of Id1 and Id3. Western blot analysis for Id1 and Id3 on A549 cells treated with Dorsomorphin and LDN.

Next it was determined whether basal BMP activity regulates the expression of Id family members in lung cancer cell lines. By quantitative RT-PCR, Dorsomorphin, DMH1, and DMH2 significantly decreased Id1, Id2, and Id3 expression in the A549 and H1299 cell lines (FIG. 2A-B). A greater reduction in the expression of Id family members was seen in H1299 cells in comparison to A549 cells. By Western blot analysis, Dorsomorphin, DMH1, DMH2, and LDN caused a decrease in protein levels of Id1 and Id3 in A549 and H1299 cells (FIGS. 2C-D and 7). The BMP antagonists decreased the expression of Id family members within 12 hours that persisted for at least 48 hours. These studies show that Id family members are regulated by a basally active BMP signaling cascade in lung cancer cells.

Figure 3:
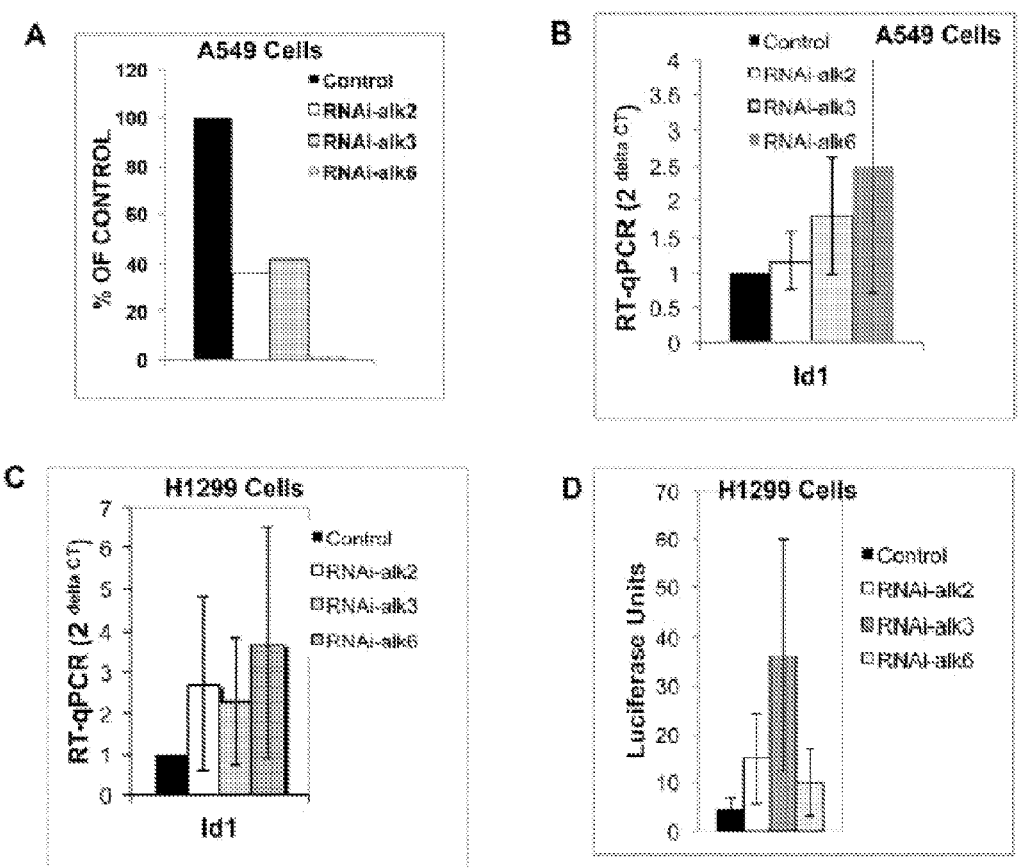
FIG. 3 illustrates that multiple BMP type I receptors mediate BMP signaling in lung cancer cell lines. (A) A549 cells were transfected with siRNA for alk2, alk3, and alk6 or siRNA control. After 48 hours quantitative RT-PCR was performed for alk2, alk3, and alk6. (B) A549 and (C) cells were transfected with siRNA for alk2, alk3, and alk6 or siRNA control. After 48 hours quantitative RT-PCR was performed for Id1. The data represents the mean of 3 experiments with expression levels normalized to GAPDH. (D) H1299 cells were co-tranfected with BRE-luciferase reporter and siRNA for a single type I BMP receptor. After 48 hours luciferace activity was measured. Data is reported as the mean of at least 3 independent experiments.

The type I BMP receptors that mediate Id expression in lung cancer cell lines was examined. By quantitative RT-PCR, the expression of the type I BMP receptors was examined. Alk1 was not expressed in either A549 or H1299 cells (FIG. 9A). As expected, alk1 was expressed in human endothelial cells (data not shown). Alk2, alk3, and alk6 mRNA is expressed in A549 and H1299 cells. There tended to be higher levels of expression of the type I receptors in A549 cells in comparison to H1299 cells (FIG. 9A). Using RNAi, the expression of each type I receptor was reduced by greater than 60% in both the cells lines (FIG. 3A and data not shown). Decreasing the expression of any single type I BMP receptor did not decrease the expression of Id1 in either the A549 or H1299 cell lines. There was variability in these experiments but silencing of only one BMP receptor caused an increased in the expression of Id1 (FIG. 3B). To further examine BMP receptor signaling, each receptor was silenced and Smad 1/5/8 activity determined using the BRE-luciferase assay. Silencing of one BMP type I receptor led to an increase Smad-1/5/8 activity (FIG. 3C). Silencing a combination of any two BMP type I receptors caused either a small decrease in Id1 expression or increased Id1 expression. The greatest decrease in Id1 expression occurred when alk2, alk3, and alk6 were silenced. Quantitative RT-PCR confirmed that all 3 type I BMP receptors were silenced with the triple knockdown experiments (FIG. 9B). These data suggest that a blockade of all type I BMP receptors is required to effectively inhibit BMP signaling in lung cancer cells.

In the C2C12 mouse myoblast cell line, DMH1 inhibited alk2 and alk3 activity but had negligible inhibitory effects on alk6. DMH2 is known to inhibit alk2 and LDN effectively inhibits alk2, alk3, and alk6. To test receptor selectivity of DMH1 and DMH2 in lung cancer cells, constitutively active alk3 or alk6 was co-transfected with the BRE-luciferase reporter into H1299 cells. DMH1 and DMH2 both caused a significant inhibition of ca-alk3. DMH1 partially inhibited alk6 but not as effectively as DMH2. LDN inhibition of alk3 and alk6 was very similar to that of DMH2.

Figure 4:
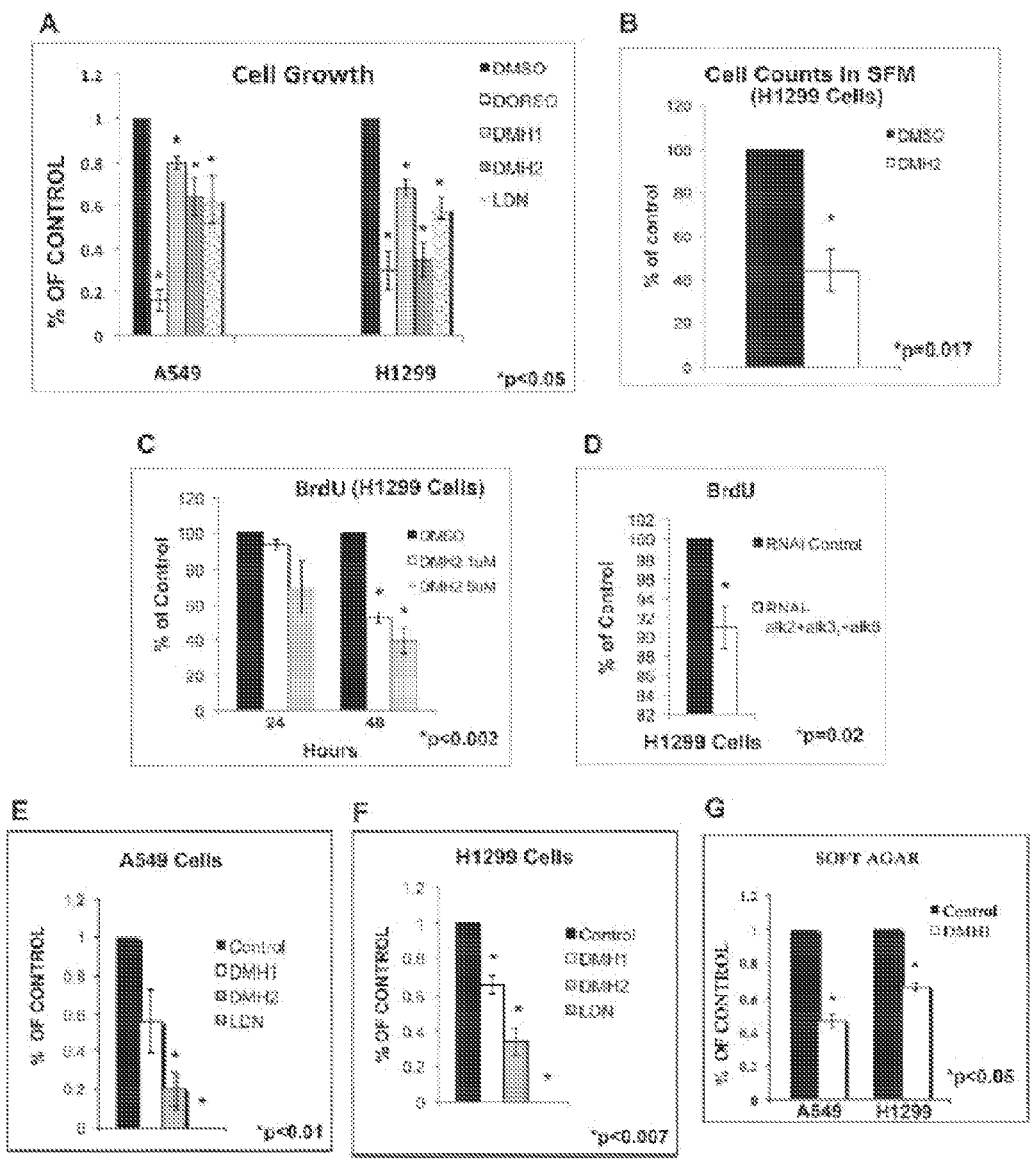
FIG. 4 shows antagonizing BMP type I receptors decreases cell growth, proliferation, and clonogenicity of lung cancer cell lines. (A) A549 and H1299 cells cultured in DMEM 5% FCS were treated with DMSO, 10 µM Dorsomorphin, 1 µM DMH1, 1 µM DMH2, or 1 µM LDN for 7 days and cell counts performed. (B) H1299 cells cultured in SFM were treated with DMSO or 1 µM DMH2 for 7 days and cell counts performed. (C) BrdU incorporation of H1299 cells treated with DMSO or 1 µM or 5 µM DMH2 for 24 and 48 hours. (D) BrdU incorporation of H1299 cells transfected with siRNA targeting alk2, alk3, and alk6 or siRNA control. (C-D) Data is the mean of 3 experiments in triplicate reported as the percent of control treated cells. (E-F) Colony growth of A549 and H1299 cells treated with 1 µM DMSO or 1 µM of selective BMP receptor antagonist. The data shows the mean of at least 3 independent experiments reported as the percent of control. (G) DMH1 decreases anchorage independent growth of lung cancer cell lines. A549 and H1299 cells in soft agar were treated with 1 µM DMSO or 1 µM DMH1 for 2 weeks and the number of colonies counted. The data shown is the mean of 3 independent experiments reported as the percent of control.

Next, the effects of blocking BMP type I receptors on cell growth and tumorigenicity was examined. BMP receptor antagonists caused a significant reduction in cell growth in both the A549 and H1299 cell lines. Dorsomorphin induced the most significant decrease in cell growth (FIG. 4A). Of the more selective BMP antagonists, DMH2 and LDN caused more growth inhibition than DMH1 (FIG. 4A). BMP receptor antagonists also decreased clonigenic growth of the A549 and H1299 cell lines (FIG. 4E-F). Clonigenic growth was inhibited more by DMH2 and LDN than DMH1. To further assess the effects of DMH1 on tumorigenicity anchorage independent growth was examined. DMH1 significantly reduced anchorage independent growth in both A549 and H1299 cells (FIG. 10). These data show that basally active BMP signaling in lung cancer cells promotes cell growth and tumorigenicity.

Figure 5:
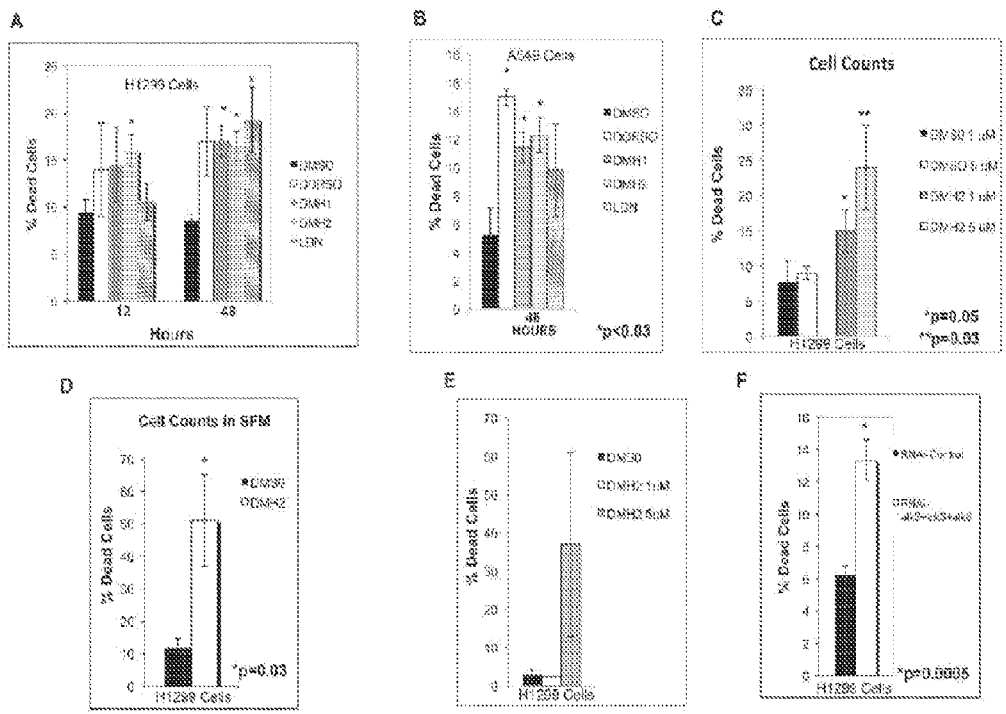
FIG. 5 shows inhibition of type I BMP receptors in lung cancer cell lines induces cell death. (A-B) H1299 and A549 cultured in DMEM 5% FCS were treated with DMSO or a BMP receptor antagonist (10 µM Dorsomorphin or 1 µM of selective antagonist). The percentage of cells that take up ethidium bromide was then determined. The data is reported as the mean of at least 3 independent experiments. (C) H1299 cells cultured in DMEM 5% FCS were treated with DMSO, 1 µM and µ5 M of DMH2 for 4 days, stained with typan blue, and cell counts performed. Data represents the mean of 4 experiments reported as the percent dead cells. (D) H1299 cells cultured in SFM were treated with DMSO or 1 µM of DMH2 for 4 days, stained with typan blue, and cell counts performed. Data represents the mean of 5 experiments reported as percent dead cells. (E) Cell death was determined using flow cytometry detecting uptake of an amine-reactive fluorescent dye in H1299 cells treated with DMSO or DMH2 for 4 days. Data represent the mean of 3 independent experiments. (F) The H1299 cells were transfected with siRNA targeting control, alk2, alk3, or alk6. After 2 days the percentage of cells staining for ethidium bromide was determined. The data is reported as the mean of 6 independent experiments.

The effect of BMP signaling on cell survival was examined. Cell death was examined using fluorescent microscopy. Ethidium bromide is only taken up by cells that lost membrane integrity, which occurs with cells that die by necrosis or apoptosis. BMP receptor antagonists induced cell death within 12 hours and by 48 hours all of the antagonists caused a significant increase in the percentage of dead cells (FIG. 5 A-B). Cell death was also examined by video time-lapse microscopy. The number of dead cells was quantified in still frame images. All the BMP receptor antagonists caused an approximately 2-fold increase in the number of dead cells. To further verify that BMP antagonists induce cell death by inhibition of BMP signaling, triple knockdown of alk2, alk3, and alk6 was performed. Silencing of alk2, alk3, and alk6 caused an approximately 2-fold increase in the percentage of death cells in comparison to controls (FIG. 5F). By Western blot analysis, the activation of caspase 3 by the BMP receptor antagonists was not detected. These data show that inhibition of BMP signaling in lung cancer cells induces cell death by a mechanism other than apoptosis.

To access whether the down regulation of Id1 mediates the anti-tumorigenic effects observed with the inhibition of BMP signaling, Id1 was stably expressed in H1299 cells. Forced expression of Id1 did not prevent the decrease in cell growth or clonigenicity induced by BMP receptor antagonists, suggesting that Id1 is not sole mediator of BMP signaling in lung cancer cells (FIG. 11).

One or more of the BMP family members are aberrantly expressed in many carcinomas including those arising from the lung, breast, prostate, ovarian, esophageal, and colon carcinomas. BMP-2 is highly expressed in the majority of NSCLC. BMP-4, BMP-6, and GDF-6 are also expressed in NSCLC. BMP-2, BMP-4 and GDF-5 bind to alk3 and alk6 with high affinity. BMP-6 and BMP-7 bind more efficiently to alk2 and alk3. BMP-2/4 can also signal though alk2 and BMP-6/7 through alk6. There are several types of BMP receptors, which complex with the different type I receptors. Activation of the BMP receptors may occur from self-autonomous activation of the BMP receptors by ligands secreted from the cell. Preformed type I and type II BMP receptor oligomers also activate BMP signaling independent of a ligand. The potential redundancy of the BMP signaling cascade in cancer suggests that multiple BMP receptors mediate signaling.

The studies suggest that the inhibition of all functional type I BMP receptors is required to cause a significant reduction in BMP signaling in lung cancer cells Inhibition of a single BMP type I receptor was not sufficient to block BMP signaling and may even lead to activation of Smad 1/5/8. Silencing of alk2, alk3, and alk6 was required to significantly block BMP signaling in lung cancer cell lines. DMH1 inhibits alk2 and alk3 with partial inhibition of alk6. DMH2 and LDN inhibit alk2 and alk3 and induced a greater blockade of alk6 than DMH1. DMH1 decreased Smad 1/5/8 activity and the expression of Id family members similar to that of DMH2 and LDN. Therefore, inhibition of alk2, alk3, and with at least partial blockade of alk6 is sufficient to inhibit Smad 1/5/8 activity in lung cancer cells. DMH1, DMH2, and LDN are specific BMP type I receptor antagonists that effectively inhibit Smad 1/5/8 signaling in lung cancer cells in vitro.

The studies provide important new insights on the role of BMP signaling in cancer. Disclosed herein is evidence that basally active BMP signaling regulates growth and survival of cancer cells. Antagonizing type I BMP receptors in lung cancer cell lines induced cell death. Cells dying from antagonizing BMP signaling demonstrated morphological features of apoptotic cell death with cell shrinkage and chromatin condensation. During development BMP can either induce or inhibit programmed cell death. However, activation of caspase-3 was not detected in the studies so apoptotic cell death was not confirmed. It is possible the number of cells that died was too small to be detected by Western blot analysis or that BMP inhibition triggers apoptosis by caspase-3 independent mechanisms. BMP could also regulate other mechanism of cell survival. Inhibition of BMP signaling also decreased cell growth and clonigenic growth of lung cancer cells. DMH2 and LDN are more potent inhibitors of alk6 than DMH1, which could represent a potential mechanism they induced a greater reduction in cell growth and clonigenicity. Since Smad 1/5/8 inhibition was the same between the different antagonists, it suggests that growth inhibition might occur in part through Smad 1/5/8 independent mechanisms. However, it is possible that DMH2 and LDN may have a greater affinity to the BMP receptors, which caused a more sustained inhibition of BMP signaling.

As disclosed herein, it was shown for the first time that basal BMP activity in lung cancer cells is an essential regulator of the expression Id1, Id2, and Id3. Since the Id family members promote tumorigenesis in so many types of cancers inhibiting there expression may have important therapeutic implications. In the studies, forced expression of Id1 did not overcome the growth suppressive effects induced by BMP antagonists. This suggests that Id1 is not the sole mediator of BMP signaling in cancer cells. It is likely that lung cancer cells are not dependent only on Id1 to regulate cell growth and survival but also utilize Id2 and Id3. The stimulation of cell growth, invasion, and metastasis has been attributed to Id1, Id2, and Id3. Id4 is thought to act as a tumor suppressor. In breast cancer, silencing both Id1 and Id3 caused a significantly greater reduction in tumor initiation and lung colonization than knockdown of either Id1 or Id3 alone. Therefore, an antagonist that inhibits Id1, Id2, and Id3 may be required to treat certain types of carcinomas.

Recent studies using monoclonal antibodies have suggested that Id expression may be confined to specific cell populations. In breast cancer, Id1 and Id3 are expressed only in triple negative tumors (estrogen −, progesterone −, and Her2Neu−). Id1 is frequently over-expressed in NSCLC, occurring in 70% of squamous and 50% of adenocarcinomas. Id2 is also over-expressed in most NSCLC and the expression of Id3 has not been reported. Further studies can be conducted in order to determine whether Id family members are expressed in specific cell populations in lung and other carcinomas.

The studies show that BMP signaling promotes cell growth, survival, and clonigenicity of lung cancer cells. BMP signaling cascade is an essential regulator of the expression of Id family members in lung cancer cells. The growth promoting effects of BMP signaling can be inhibited by specific small molecule antagonists of the type I BMP receptors. BMP receptor antagonists may represent a means to treat cancers that depend on the BMP and/or Id family members to sustain tumor viability.

Example 2

The Bone Morphogenetic Proteins (BMPs) are members of the Transforming Growth Factor superfamily (TGF). BMPs are phytogenetically conserved proteins required for embryonic development from insects to humans. Approximately 20 BMP ligands have been identified and categorized into several subclasses. BMP-2 and BMP-4 share 92% homology and have interchangeable biological activity. BMPs are secreted proteins that signal through transmembrane serine/threonine kinases called type I and type II receptors [1]. The type I receptors are alk1, alk2 (ActR-1), alk3 (BMPR-IA), and alk6 (BMPR-IB) [1]. The type II receptors are BMPR-II and activin type II receptors ActR-II and AcR-IIB [1]. BMP receptors are promiscuous, and can be activated by several BMP ligands [1,2]. Each BMP ligand is also capable of activating different receptors [1,2]. Binding of the BMP ligands to the type I receptor leads to phosphorylation by the constitutively active type II receptor. The receptor complex phosphorylates Smad-1/5, which then activates the transcription of downstream target genes [3].

During embryonic development, BMPs regulates cell fate decisions, cell survival, and vasculogenesis [4,5,6,7], processes that are also common in carcinogenesis. In fact, BMP-2 is over-expressed in 98% of NSCLC and other carcinomas [8,9]. BMP expression inversely correlates with survival[10] and high expression is associated with metastatic spread [11,12]. BMP-2 enhances tumor angiogenesis [13,14,15] and stimulates tumor invasion[8]. Ectopic expression of BMP-2 in A549 lung cancer cells greatly enhanced metastatic growth in a murine model of lung cancer following tail vein injection[16]. Studies using recombinant BMP proteins or knockdown of a single BMP receptor have suggested that BMP signaling in cancer cells does not promote cell growth and may even act as a tumor suppressor (16-19). The effects of inhibiting multiple BMP receptors on cell growth and survival in cancer cells has not been examined. Therefore, the biological significance of a basally active BMP signaling cascade in cancer cells is not known.

During development the inhibitors of DNA binding/differentiation (Id) are direct mediators of BMP signaling. There are 4 Id family members (Id1, Id2, Id3, and Id4). BMP response elements (BRE) on the Id1, Id2, and Id3 promoters are activated by Smad 1/5/8 (20-23). The Id proteins inhibit lineage commitment by binding and sequestering basic HLH transcription factors [17]. Id family members have been implicated in oncogenic transformation in several types of cancers [18] [19,20]. Id1 has been reported to regulate invasion, proliferation, survival, and the metastatic spread of cancer cells [18,21,22]. Id family members are frequently expressed in non-small cell lung carcinomas [23,24] and over-expression is associated with a shorter disease free survival[25]. These studies suggest that targeting signaling pathways, which regulate the expression of Id family members may have important therapeutic implications. Although recombinant BMP2 proteins induce a transient increase in the expression of Id1 in lung cancer cells [8], the role of the BMP signaling cascade in regulating the basal expression levels of the Id family members in cancer cells has not been elucidated.

The aim of this study was to determine in lung cancer cell lines, which have not been stimulated with a recombinant BMP protein, whether cells have a basally active BMP signaling and determine its effect on cell growth, survival, and expression of Id family members. Selective BMP type I receptor antagonists and siRNA targeting the BMP type I receptors reveals that basally active BMP signaling in lung cancer cell lines is growth promoting and an important regulator of the expression of Id family members. BMP signaling is mediated through more than one type I BMP receptor. DMH2 caused the greatest inhibition of BMP signaling and induced the greatest reduction of cell growth and expression of Id family members.

Results

BMP type I receptor antagonists decrease Smad 1/5/8 signaling. Using a BMP-responsive luciferase reporter (BRE-Luc), the effects of the different BMP type receptor antagonists on Smad 1/5/8 activity in H1299 cells were examined. Dorsomorphin, DMH1, DMH2, and LDN all caused a significant decrease in Smad 1/5/8 activity in H1299 cells (FIG. 1A). Immunoblot analysis revealed that selective BMP type I receptor antagonists decrease phosphorylation of Smad 1/5/8 in H1299 and A549 cells (FIG. 1B and FIG. 12). Phosphorylation of Smad 1/5/8 was decreased within 24 hours of treatment and persisted for at least 48 hours thereafter.

BMP type I receptor antagonists decrease expression of Id family members. Quantitative RT-PCR was used to determine whether the BMP signaling cascade regulates the expression of Id family members in lung cancer cell lines. Dorsomorphin, DMH1, and DMH2 significantly decreased Id1, Id2, and Id3 expression in A549 and H1299 cell lines (FIG. 2A-B). The BMP antagonists caused a greater reduction of Id family members in the H1299 cells compared to A549 cells. By Western blot analysis, Dorsomorphin, DMH1, DMH2, and LDN caused a decrease in protein levels of Id1 and Id3 in A549 and H1299 cells (FIG. 2C-D and FIG. 13). The BMP antagonists decreased the expression of Id family members within 12 hours that persisted for at least 48 hours. DMH1 and DMH2 caused a greater reduction of Id1 in H1299 cells compared to A549 cells. DMH2 consistently caused a greater reduction of Id1 protein expression than DMH1. To determine whether the monoclonal Id antibodies used for Western blot were detecting Id1 and Id3, knockdown of Id1 and Id3 was performed. Western blot analysis confirmed that the Id1 and Id3 antibodies were detecting Id1 and Id3 proteins respectively (FIG. 14).

Figure 8:
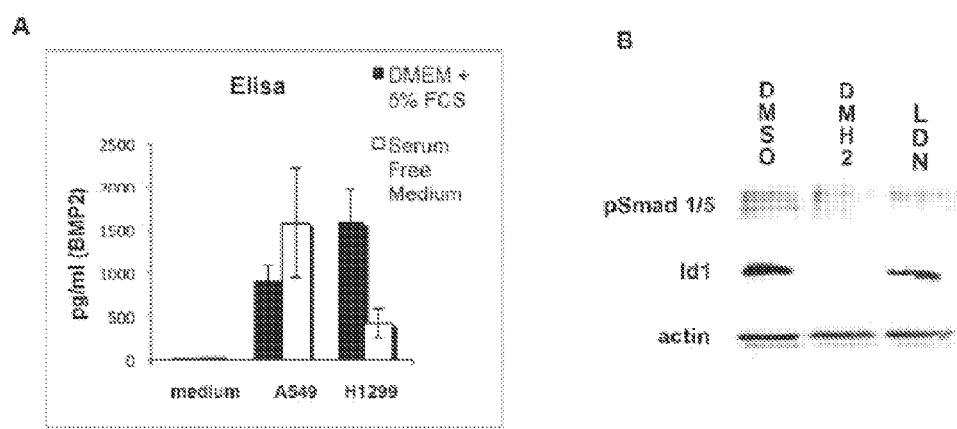
FIG. 8 shows that lung cancer cell lines secrete BMP2. (A) A BMP2 Elisa was performed on DMEM 5% FCS and SFM in the absence of cultured cells (medium). A BMP2 Elisa was performed on DMEM 5% FCS and SFM cell culture medium containing A549 and H1299 cells for 48 hours. Experiments represent the mean of at least 5 experiments performed in triplicate. (B) Lung cancer cell lines cultured in SFM are responsive to BMP antagonists. H1299 cells cultured in SFM were treated with 1 μM DMSO, 1 μM of DMH2 or 1 μM of LDN for 48 hours and Western blot analysis performed.

BMP signaling is regulated in a self-autonomous manner. Prior studies have shown that lung cancer cell lines produce the mature BMP2 protein, which is the active form {Langenfeld, 2003 #625}. To ensure that lung cancer cells secrete BMP2, an ELISA of the cell culture media was performed. BMP2 protein was not detected in DMEM 5% fetal calf (FCS) or in serum free medium (FIG. 8A). BMP2 was detected in the medium when lung cancer cell lines were cultured in either SFM or DMEM 5% FCS (FIG. 8A). Since small but undetectable levels of BMP2 could be in FCS, the effects of BMP receptor antagonists on the regulation of BMP signaling was examined in SFM. Phosphorylated Smad 1/5 and Id1 expression was detected in H1299 cells cultured in serum free medium (FIG. 8B). BMP type I receptor antagonists decreased pSmad 1/5 and Id1 expression (FIG. 8B) of H1299 cells cultured in SFM (FIG. 8B). These studies suggest that basal BMP activity of lung cancer cell lines in cell culture is stimulated in a self-autonomous manner, which can be inhibited by antagonizing BMP type I receptors.

Multiple BMP type I receptors mediate signaling. Next, it was assessed whether a specific BMP type I receptor mediates basally active BMP signaling in lung cancer cell lines. By quantitative RT-PCR, the expression of BMP type I receptors was examined. Alk1 was not expressed in either A549 or H1299 cells (FIG. 9A). As expected, alk1 was expressed in human endothelial cells (data not shown) Alk2, alk3, and alk6 mRNA are expressed in A549 and H1299 cell lines (FIG. 9A). Using siRNA, the expression of each type I receptor was reduced by greater than 40% (FIG. 9B). To test specificity of the siRNA, knockdown of each type I receptor was performed and RT-PCR performed for alk2, alk3, and alk6. There was no more than a 25% "off-target" silencing of the other BMP type I receptors with each specific knockdown (FIG. 9C). Quantitative RT-PCR showed that silencing of alk2 or alk3 in the H1299 cells caused an approximately 20-25% decrease in the expression of Id1 mRNA (FIG. 9D), while silencing of alk6 tended to cause an increase in Id1 expression. Silencing both alk2 and alk3 caused a significantly greater decrease in Id1 expression than knockdown of either receptor alone (FIG. 9D). Western blot analysis showed that knockdown of a single type IA receptor alone did not decrease Id1 expression (FIG. 9E). Silencing of both alk2 and alk3 or silencing of alk2, alk3, and alk6 did cause a decrease in Id1 protein expression (FIG. 9E).

A second set of siRNA targeting each BMP type I receptor was used to further assess BMP signaling. These siRNA also caused a significant decrease in expression of the targeted receptor (FIG. 3A). Again, knockdown of a single type I BMP receptor was not sufficient to decrease Id1 expression in either the A549 and H1299 cells (FIG. 3B-C). To further examine BMP receptor signaling, each receptor was silenced and Smad 1/5/8 activity determined using the BRE-luciferase assay. Silencing only one BMP type I receptor did not cause a decrease in Smad-1/5/8 activity (FIG. 3D). These data suggests that BMP signaling is mediated through more than one type I BMP receptor in lung cancer cell lines.

In the C2C12 mouse myoblast cell line, DMH1 inhibited alk2 and alk3 activity but was reported to have negligible inhibitory effects on alk6 [26]. DMH2 is known to inhibit alk2 and LDN effectively inhibits alk2, alk3, and alk6 [26]. To test receptor selectivity of DMH1, DMH2, and LDN in lung cancer cells, constitutively active alk3 (ca-alk3) or alk6 (ca-alk6) was co-transfected with the BRE-luciferace reporter into H1299 cells (FIG. 9F). DMH2 caused a greater reduction of alk3 activity than DMH1 and LDN in the H1299 cells. The BMP antagonists caused some inhibition of alk6 but less than that seen for alk3 (FIG. 9F). DMH2 also caused more inhibition of alk6 than DMH1 and LDN (FIG. 9F).

Inhibition of BMP type I receptors decreases cell growth. Next, the effects of blocking BMP type I receptors on cell growth was examined by performing cell counts. BMP type I receptor antagonists caused a significant reduction in the number of cells after 7 days in both the A549 and H1299 cell lines (FIG. 4A). The selective BMP receptor antagonists caused a greater reduction in cell growth in the H1299 cells compared to A549 cells. DMH2 caused significantly more growth inhibition than DMH1 in both cell lines (FIG. 4A). DMH2 also caused a significant inhibition of cell growth of H1299 cells cultured in SFM (FIG. 4B). Proliferation was examined by determining bromodeoxyuridine (BrdU) incorporation. DMH2 caused a dose dependent decrease in proliferation of the H1299 cells within 24 hours (FIG. 4C). A more profound effect was seen at 48 hours (FIG. 4C). Knockdown of all 3 type I BMP receptors (alk2, alk3, and alk6) in the H1299 cells also caused a significant decrease in BrdU incorporation (FIG. 4D).

BMP type I receptor antagonists decrease clonogenic growth. BMP receptor antagonists decrease clonogenic growth of the A549 and H1299 cell lines (FIG. 4E-F). Clonogenic growth was inhibited more by DMH2 and LDN than DMH1. To further assess the effects of DMH1 on clonogenic growth, anchorage independent growth was examined. DMH1 significantly reduced anchorage independent growth in both A549 and H1299 cells (FIG. 4G). These data show that basally active BMP signaling stimulates proliferation and enhances clonogenic growth of lung cancer cells.

Inhibition of BMP type I receptors induces cell death. The effect of BMP signaling on cell survival was examined. Cell death was quantified using an ethidium bromide uptake assay. Ethidium bromide is only taken up by cells that have lost membrane integrity, which occurs when cells are dying by necrosis or apoptosis [27]. BMP type I receptor antagonists induced cell death in the H1299 cells within 12 hours, and by 48 hours all of the antagonists caused a significant increase in the percentage of dead cells (FIG. 5A). Within 48 hours, Dorsomorphin, DMH1, and DMH2 caused a significant increase in cell death in the A549 cells. To further assess whether BMP antagonists induce cell death, H1299 cells cultured in DMEM 5% FCS were treated with DMH2 for 4 days and cells the percentage of dead cells determined by trypan blue staining DMH2 caused a significant increased in cell death, which was dose dependent (FIG. 5C). The percentage of dead cells was even higher in H1299 cells cultured in SFM (FIG. 5D). An amine-reactive fluorescent dye was used to detect cell death, which also showed that DMH2 induced cell death in the H1299 cells (FIG. 5E). To further verify that BMP antagonists induce cell death by inhibition of BMP signaling, triple knockdown of alk2, alk3, and alk6 receptors was performed. Knockdown of alk2, alk3, and alk6 receptors caused an increase in the percentage of dead cells in comparison to siRNA control treated cells (FIG. 5F). These studies show that inhibiting the activity of the BMP type I receptors induces cell death in lung cancer cells.

Id1 and Id3 regulate cell growth and survival in lung cancer cell lines. Next, it was examined whether Id1 and Id3 regulated cell survival and growth of lung cancer cell lines. Knockdown of Id1 or Id3 in H1299 cells caused a significant increase in the percentage of dead cells as determined by ethidium bromide staining (FIG. 6A). Cell counts using trypan blue staining also showed that knockdown of either Id1 or Id3 decreased cell growth (FIG. 6B) and caused an increase in the percentage of dead cells in comparison to controls (FIG. 6C). These studies suggest that reduction of Id expression is the mechanism by which BMP receptor antagonists induce cell death.

Discussion

BMP family members are aberrantly expressed in many carcinomas including those arising from the lung, breast, prostate, ovarian, esophageal, and colon carcinomas [28,29]. BMP-2 is expressed approximately 17 fold higher in NSCLC compared to normal lung or benign lung tumors [9]. BMP-4, BMP-6, and GDF-5 are also expressed in NSCLC but less frequently and by a lower amount than BMP-2 [9]. BMP-2, BMP-4, and GDF-5 bind to alk3 and alk6 with high affinity [1]. BMP-6 and BMP-7 bind more efficiently to alk2 and alk3 [1]. BMP-2/4 can also signal through alk2 and BMP-6/7 through alk6 [2]. Activation of the BMP receptors occurs from secreted ligands. Preformed type I and type II BMP receptor oligomers can also activate BMP signaling independent of a ligand [30].

The data suggests that BMP signaling is mediated in lung cancer cells through multiple BMP type I receptors. Herein it is shown that alk2, alk3, and alk6 are expressed in lung cancer cell lines. A prior report showed that alk3 and alk6 are expressed in NSCLC [8]. The expression of alk2 in primary NSCLC has not been reported. Knockdown of a single BMP type I receptor was not sufficient to inhibit BMP signaling and its regulation of the downstream target Id1. Silencing of more than one type I BMP receptors was required to inhibit BMP signaling in lung cancer cell lines. DMH2, which caused the greatest inhibition of alk3 and alk6 also induced the greatest reduction in the expression of the downstream target Id1. DMH2 is also reported to be a potent antagonist of alk2 [26]. In the H1299 cell line, inhibition of alk2 and alk3 was sufficient to reduce Id1 expression. Knockdown of alk2, alk3, and alk6 also decreased Id1 protein expression in H1299 cells. These studies suggest that an antagonists targeting all function type I BMP receptors in cancer cells causes the most significant suppression of BMP signaling. Since DMH2 is a selective BMP type I antagonist with very good in vitro activity it is an excellent candidate drug to study its efficacy in a lung tumor xenograft model.

The studies support that the BMP signaling cascade is growth promoting in cancer. Antagonizing BMP type I receptors in lung cancer cell lines caused significant growth inhibition, decreased clonogenic growth, and induced cell death. BMPs having a growth-promoting role in cancer is consistent with its role as an essential growth enhancing morphogen during development [31] [32]. Prior studies suggesting that BMP signaling is growth suppressive or only has a minimal effect on cell growth may be explained by differences in study design [33,34,35,36]. Recombinant BMP proteins produce a transient response in cell lines and are known to induce the expression of BMP antagonists [37]. The induction of BMP antagonists may attenuate any potential for an enhanced mitogenic response. The studies suggest that the knockdown of a single BMP receptor may not cause a sufficient inhibition of BMP signaling in some cell lines. Blocking the basal activity of all functional BMP type I receptors effectively decreases signaling and has provided a new insight into the role of BMP signaling in cancer.

It is shown that the basal BMP activity in lung cancer cell lines is an essential regulator of Id1, Id2, and Id3 expression. Since the Id family members promote tumorigenesis in so many types of cancers, inhibiting their expression may have important therapeutic implications. Knockdown of Id1 or Id3 induced cell death and decreased cell growth, suggesting that the regulation of Id family members is an essential survival mechanism mediated by the BMPs. The stimulation of cell growth, invasion, and metastasis has been attributed to Id1, Id2, and Id3 [38,39]. Id4 is thought to act as a tumor suppressor [40,41,42]. In breast cancer, silencing both Id1 and Id3 caused a significantly greater reduction in tumor initiation and lung colonization than knockdown of either Id1 or Id3 alone [18]. Therefore, an antagonist that inhibits Id1, Id2, and Id3 may be required to treat carcinomas that are dependent on Id signaling.

Recent studies, using monoclonal antibodies, have suggested that the expression of Id family members is confined to a specific population of cancer cells. In breast cancer, Id1 and Id3 are expressed predominately in triple negative tumors (estrogen –, progesterone –, and Her2Neu–) [18]. Id1 is frequently over-expressed in NSCLC, occurring in 70% of squamous and 50% of adenocarcinomas [23]. Id2 is also over-expressed in most NSCLC and the expression of Id3 has not been reported [24]. It is not know whether Id family members are expressed in a specific cell population in lung carcinomas. Reports have suggested that specific population of cancer cells have the capacity to self-renew. Since BMP signaling and Id family members regulate self-renewal and cell fate decisions of stem cells, it will be of interest to determine there role in the regulation of cancer cells with stem cell like characteristics.

The studies show that BMP signaling promotes cell growth, survival, and clonogenicity of lung cancer cells. The BMP signaling cascade is an essential regulator of the basal expression of Id family members in lung cancer cell lines. The growth promoting effects of BMP signaling can be inhibited by specific small molecule antagonists of the type I BMP receptors. BMP receptor antagonists may represent a novel means to treat lung and other cancers that depend on the BMP and/or Id family members to sustain tumor viability.

Methods

Plasmids. Constitutively active alk3 and alk6 constructs in mammalian vectors were a gift from Joan Massague (New York, N.Y.) [43]. BRE-luciferase plasmid containing Smad 1/5/8 binding sites derived from the Id1 promoter [44] was a gift from Isaak Kim (UMDNJ Medical School). The Id1 expression vector (PLXSN Id-1) and control vector (PLXSN) was a gift from Pierre Desprez (California Pacific Medical Center)

Cell Culture and Reagents. The cell lines, A549 and H1299 lung cancer cell lines were cultured in Dulbecco's Modified Eagle's medium (DMEM, Sigma Aldrich, St Louis, Mo., USA) with 5% fetal bovine serum (FBS) containing 1% penicillin/streptomycin, and 1% glutamine. The A549 and H1299 cell lines were obtained from ATCC. Cells were kept in a humidified incubator with 5% CO2 at 37° C. [45]. Dorsomorphin (compound C) was purchased from Sigma. Dorsomporphin analogues DMH1, DMH2, and LDN were a kind gift from Charles Hong (Vanderbelt University). Dorsomorphin is a small molecule antagonist of the BMP type I receptors [46]. Dorsomorphin analogues DMH1, DMH2, [47] and LDN [48] are more specific and potent antagonists of the type I BMP receptors. LDN has less AMP kinse activity than Dorsomorphin (32). DMH1 and DMH2 are even more specific analogues that have less activity for VEGF II, AMP kinase, TGFβ receptor alk5, and platelet-derived growth factor receptor-β than Dorsomorphin and LDN (33).

Quantification of Gene Expression. RNA was extracted using the RNeasy kit as per the manufacturer's instructions (Qiagen, Valencia, Calif.). DNAase was used to remove any DNA contamination. cDNA was generated using Advantage RT for PCR kit (BD BiosciencesClontech, Palo Alto, Calif.). Quantitative PCR was performed with the Stratagene Mx3005p (Agilent Technologies) and predesigned validated Taq-Man gene expression assays according to the manufacturer's specifications (Applied Biosystems, Foster City, Calif.). Reference numbers used are: GAPDH (Hs99999905_m1), ACVRL1 (alk1) (Hs00163543_m1), ACVR1A (alk2) (Hs00153836_m1), BMR1A (alk3) (Hs00831730_s1), BMPR1B (alk6) (Hs00176144_m1), Id1 (Hs00357821_g1), Id2 (Hs00747379_m1), and Id3 (Hs00171409-m1). Negative control included all reagents except cDNA. Expression was normalized to GAPDH using the formula $2^{\Delta CT}$.

Transient Gene Knockdown. Silencer Select Validated and Pre-designed siRNA were used to target the type I BMP receptors alk2, alk3, and alk6. The siRNA ID numbers used are: alk2 (s975-validated), alk3 (s280-Pre-designed), and alk 6 (s2041-Pre-designed). Silencer Select Negative Control siRNA (4390843) was used to confirm specificity of each targeted knockdown.

A549 and H1299 cells were transfected with siRNA using a Nucleofector II (Amaxa Biosystems, Gaithersburg, Md.) using the manufacture's Nucleofector kit T. Optimization was performed using the enhanced green fluorescent reporter (EGFP) (Clontech) expressed in the pcDNA 3.1 vector (Invitrogen), which showed approximately 80% of the cells were transfected using this transfection protocol. A total of 30 nM of siRNA was used for alk2 and alk3. For alk6 a total of 20 nM of siRNA was used. An equal amount of control siRNA was used in each experiment. The siRNA was delivered to $1 \times 10^6$ A549 and H1299 cells and cultured for 48 hours in DMEM with 5% FCS. BMP receptors and Id1 expression was measured by qPCR.

Western Blot Analysis. Total cellular protein was prepared using RIPA buffer containing a protease inhibitor cocktail and protein concentration was measured using the BCA assay as described [8]. In brief, protein was analyzed by SDS-PAGE, transferred to nitrocellulose (Schleicher and Schuell, Keene, N.H.). After blocking, the blots were incubated overnight at 4° C. with the appropriate primary antibody in Tris-buffered saline with 1% Tween (TBST) and 5% non-fat milk. Secondary antibodies were applied for 1 hour at room temperature. Specific proteins were detected using the enhanced chemiluminescence system (Amersham, Arlington Heights, Ill.). The primary antibodies that were used were rabbit monoclonal anti-pSmad 1/5/8 (Cell signaling Technology, Danvers Mass.) rabbit anti-actin, an affinity isolated antigen specific antibody (Sigma, Saint Louis, Mo.), rabbit monoclonal anti-Id1 and rabbit monoclonal anti-Id3 (Calbioreagents, San Mateo, Calif.).

Luciferase Assays. $10^6$ H1299 cells were transfected with 2 µg of BRE-luciferace plasmid using a Nucleofector II. Forty-eight hours later the cells were treated with DMSO or a BMP receptor antagonist and cell lysates were harvested 24 hours after treatment. Cells were lysed with luciferase lysis buffer (Promega). Samples were added to luciferase assay substrate (Promega) and luminsescence measured by the TD-20/20 Luminometer (Turner Designs/Turner Bio-Systems, Sunnyvale, Calif.). Control samples included luciferase assay substrate alone and luciferase assay substrate plus 1× reporter lysis buffer.

To assess the effects of antagonists on a specific type I BMP receptor, 2 µg of constitutively active ca-alk3 and ca-alk6 expression vectors were co-transfected with the BRE-luciferase reporter into H1299 cells with Nucleofector II. Control cells were co-transfected with the pcDNA3 expression vector. After 48 hours the cells were treated with DMSO or a BMP receptor antagonist for 48 hours and luminescence was measured.

To examine the effects of knockdown of a single type I BMP receptor on Smad 1/5/8 activity, H1299 cells were co-transfected with siRNA targeting alk2, alk3, or alk6 together with the BRE-luciferase reporter. Luminescence was measured 48 hours after transfection.

Cell Death Assay: A549 and H1299 cells were plated in 6 well plates with $10^6$ cells per well. Cells were treated with DMSO or a BMP receptor antagonist for 12 and 48 hours. Adherent and floating cells were harvested and incubated with 0.1 mg/ml of ethidium bromide. Immediately after staining approximately 100 cells were counted and the percentage of cells that took up ethidium bromide was determined.

Cell death was also determined using the LIVE/DEAD fixable dead cell stain kit as per manufacturer's instructions (Life Technologies, L-23101). This assay employs an amine-reactive fluorescent dye, which in compromised membranes the dye reacts with free amines on the cell interior in dead cells. H1299 cells were treated with DMH2 for 48 hours and the percentage of dead cells then detected by flow cytometry.

Cell death was also determined by treating H1299 cells with DMSO, DMH2 1 µM, and DMH2 5 µM for 7 days, floating and adherent cells were stained with trypan blue and cell counts performed. The percentage of live and dead cells was then determined.

Knockdown of all type I BMP receptors was performed in the H1299 cells by transfecting siRNA for alk2, alk3, and alk6 or control siRNA. Two days after the transfection the cells were harvested and the percentage of cells staining for ethidium bromide was determined.

Clonigenic Growth Assay. A549 and H1299 cells were plated into 6 well plates with 500 cells per well. The next day the cells were treated with DMSO or a BMP receptor antagonist for 2 weeks. The colonies were stained with Diff-Quick (IMEB Inc. San Marcos, Calif.) and the total number of colonies per well counted.

Cell Counts. A549 and H1299 cells were plated into 6 well plates with 100,000 cells per well. Cells were treated with DMSO or a BMP receptor antagonist for 7 days. The cells were detached with trypsin, stained with trypan blue, and the number of live cells counted using a hemacytometer.

BrdU Assay. Thirty-thousand H1299 cells were plated into 96 well plates. The next day the cells were treated with 1 µM DMSO, 5 µM DMSO, 1 µM DMH2, or 5 µM DMH2 for 24 and 48 hours. BrdU incorporation was measured using the Cell Proliferation ELISA, BrdU colorimetric kit as per manufacture's instruction (Roche, Indianapolis, Ohio). Cells were incubated with BrdU labeling solution for 2 hours, fixed/denatured, and BrdU located with a peroxidase-conjugated anti-BrdU antibody. Knockdown of all type I BMP receptors were performed in the H1299 cells by transfecting siRNA for alk2, alk3, and alk6 or control siRNA. Three days after transfection BrdU incorporation was determined. Studies were performed 4 times in triplicate.

Soft Agar Assay. A 1% agar mixture was prepared in sterile double-distilled water, microwaved, and cooled to 40° C. in a water bath. DMEM was also incubated at 40° C. Equal amounts of each were mixed and 1 ml added to each well of a six well plate. The base agar was allowed to solidify. A 0.7% agar mixture was prepared then cooled to 40° degrees. Cells were trypsinized and counted. Cells (2500 cells per well) were placed in pre-warmed DMEM containing DMSO or DMH1 (104/m1). The treated cells were then mixed with the 0.7% agar and 2 ml placed on top of the base agar. Once solidified, 1 ml of DMEM was placed on top of the agar. Colonies were counted four weeks later using a microscope.

BMP2 Elisa: H1299 and A549 cells were seeded into 6 well plates in duplicate at 150,000 cells/well. The cells were incubated for 4 days in either DMEM 5% FCS or SFM. Cell culture medium as also placed into wells that did not contain cells. The medium was collected and BMP2 Elisa performed as per manufacture's instructions (PeproTech, Rocky Hill, N.J.).

Statistical Analysis. The mean of the control group was compared to the mean of each treated group using a paired student t-test assuming unequal variances. Differences with p values ≤0.05 were considered statistically significant.

With reference to FIG. 15, mice were injected subcutaneously with a cell line to generate tumors. H1299 tumors of approximately 100 $mm^3$ in size were injected around the tumor with DMSO or Dorsomorphin (40 µM) 3 times weekly. Tumor size was determined 3 weeks after initiation of treatment. (n=6) As shown in FIG. 15, tumor size is reduced in response to treatment with a BMP inhibitor.

Throughout this document, various references are mentioned. All such references are incorporated herein by reference to the same extent as if each individual reference was specifically and individually indicated to be incorporated by reference, including the references set forth in the following list:

REFERENCES

1. Nickel J, Sebald W, Groppe J C, Mueller T D (2009) Intricacies of BMP receptor assembly. Cytokine Growth Factor Rev 20: 367-377.
2. Lavery K, Swain P, Falb D, Alaoui-Ismaili M H (2008) BMP-2/4 and BMP-6/7 differentially utilize cell surface receptors to induce osteoblastic differentiation of human bone marrow-derived mesenchymal stem cells. J Biol Chem 283: 20948-20958.
3. Attisano L, Wrana J L (2002) Signal transduction by the TGF-beta superfamily. Science 296: 1646-1647.
4. Pizette S, Abate-Shen C, Niswander L (2001) BMP controls proximodistal outgrowth, via induction of the apical ectodermal ridge, and dorsoventral patterning in the vertebrate limb. Development 128: 4463-4474.
5. Yang X, Castilla L H, Xu X, Li C, Gotay J, et al. (1999) Angiogenesis defects and mesenchymal apoptosis in mice lacking SMAD5. Development 126: 1571-1580.
6. Chang H, Huylebroeck D, Verschueren K, Guo Q, Matzuk M M, et al. (1999) Smad5 knockout mice die at midgestation due to multiple embryonic and extraembryonic defects. Development 126: 1631-1642.
7. Ying Q L, Nichols J, Chambers I, Smith A (2003) BMP induction of Id proteins suppresses differentiation and sustains embryonic stem cell self-renewal in collaboration with STAT3. Cell 115: 281-292.
8. Langenfeld E M, Calvano S E, Abou-Nukta F, Lowry S F, Amenta P, et al. (2003) The mature bone morphogenetic protein-2 is aberrantly expressed in non-small cell lung carcinomas and stimulates tumor growth of A549 cells. Carcinogenesis 24: 1445-1454. Epub 203 June 1419.
9. Langenfeld E M, Bojnowski J, Perone J, Langenfeld J (2005) Expression of bone morphogenetic proteins in human lung carcinomas. Ann Thorac Surg 80: 1028-1032.
10. Le Page C, Puiffe M L, Meunier L, Zietarska M, de Ladurantaye M, et al. (2009) BMP-2 signaling in ovarian cancer and its association with poor prognosis. J Ovarian Res 2: 4.
11. Yuen H F, Chan Y P, Cheung W L, Wong Y C, Wang X, et al. (2008) The prognostic significance of BMP-6 signaling in prostate cancer. Mod Pathol 21: 1436-1443. Epub 208 October 1417.
12. Park Y, Kang M H, Seo H Y, Park J M, Choi C W, et al. (1192) Bone morphogenetic protein-2 levels are elevated in the patients with gastric cancer and correlate with disease progression. Med Oncol 27: 1192-1199.
13. Langenfeld E M, Langenfeld J (2004) Bone morphogenetic protein-2 stimulates angiogenesis in developing tumors. Mol Cancer Res 2: 141-149.
14. Raida M, Clement J H, Leek R D, Ameri K, Bicknell R, et al. (2005) Bone morphogenetic protein 2 (BMP-2) and induction of tumor angiogenesis. J Cancer Res Clin Oncol 131: 741-750. Epub 205 November 2001.
15. Rothhammer T, Bataille F, Spruss T, Eissner G, Bosserhoff A K (2007) Functional implication of BMP4 expression on angiogenesis in malignant melanoma. Oncogene 26: 4158-4170. Epub 206 December 4118.
16. Langenfeld E M, Kong Y, Langenfed J (2005) Bone morphogenetic protein 2 stimulation of tumor growth involves the activation of Smad-1/5. Oncogene Epub.
17. Alani R M, Young A Z, Shifflett C B (2001) Id1 regulation of cellular senescence through transcriptional repression of p16/Ink4a. Proc Natl Acad Sci USA 98: 7812-7816. Epub 201 June 7826.
18. Gupta G P, Perk J, Acharyya S, de Candia P, Mittal V, et al. (2007) ID genes mediate tumor reinitiation during breast cancer lung metastasis. Proc Natl Acad Sci USA 104: 19506-19511.
19. Swarbrick A, Roy E, Allen T, Bishop J M (2008) Id1 cooperates with oncogenic Ras to induce metastatic mammary carcinoma by subversion of the cellular senescence response. Proc Natl Acad Sci USA 105: 5402-5407. Epub 208 March 5431.
20. Ling M T, Wang X, Zhang X, Wong Y C (2006) The multiple roles of Id-1 in cancer progression. Differentiation 74: 481-487.
21. Swarbrick A, Akerfeldt M C, Lee C S, Sergio C M, Caldon C E, et al. (2005) Regulation of cyclin expression and cell cycle progression in breast epithelial cells by the helix-loop-helix protein Id1. Oncogene 24: 381-389.
22. Li B, Tsao S W, Li Y Y, Wang X, Ling M T, et al. (2009) Id-1 promotes tumorigenicity and metastasis of human esophageal cancer cells through activation of PI3K/AKT signaling pathway. Int J Cancer 125: 2576-2585.
23. Rothschild S I, Kappeler A, Ratschiller D, Betticher D C, Tschan M P, et al. The stem cell gene "inhibitor of differentiation 1" (ID1) is frequently expressed in non-small cell lung cancer. Lung 71: 306-311. Epub 210 August 2014.
24. Rollin J, Blechet C, Regina S, Tenenhaus A, Guyetant S, et al. (2009) The intracellular localization of ID2 expression has a predictive value in non small cell lung cancer. PLoS One 4: e4158. Epub 209 January 4158.
25. Ponz-Sarvise M, Nguewa P A, Pajares M J, Agorreta J, Lozano M D, et al Inhibitor of Differentiation-1 as a Novel Prognostic Factor in NSCLC Patients with Adenocarcinoma Histology and Its Potential Contribution to Therapy Resistance. Clin 17: 4155-4166. Epub 2011 May 4153.
26. Hao J, Ho J N, Lewis J A, Karim K A, Daniels R N, et al. In vivo structure-activity relationship study of dorsomorphin analogues identifies selective VEGF and BMP inhibitors. ACS Chem Biol 5: 245-253.
27. Leite M, Quinta-Costa M, Leite P S, Guimaraes J E (1999) Critical evaluation of techniques to detect and measure cell death—study in a model of UV radiation of the leukaemic cell line HL60. Anal Cell Pathol 19: 139-151.
28. Kiesslich T, Berr F, Alinger B, Kemmerling R, Pichler M, et al. Current Status of Therapeutic Targeting of Developmental Signalling Pathways in Oncology. Curr Pharm Biotechnol 2011: 24.
29. Ye L, Mason M D, Jiang W G Bone morphogenetic protein and bone metastasis, implication and therapeutic potential. Front 16: 865-897.
30. Nohe A, Hassel S, Ehrlich M, Neubauer F, Sebald W, et al. (2002) The mode of bone morphogenetic protein (BMP) receptor oligomerization determines different BMP-2 signaling pathways. J Biol Chem 277: 5330-5338. Epub 201 November 5319.
31. Lawson K A, Dunn N R, Roelen B A, Zeinstra L M, Davis A M, et al. (1999) Bmp4 is required for the generation of primordial germ cells in the mouse embryo. Genes Dev 13: 424-436.
32. Kishimoto Y, Lee K H, Zon L, Hammerschmidt M, Schulte-Merker S (1997) The molecular nature of zebrafish swirl: BMP2 function is essential during early dorsoventral patterning. Development 124: 4457-4466.
33. Tada A, Nishihara T, Kato H (1998) Bone morphogenetic protein 2 suppresses the transformed phenotype and restores actin microfilaments of human lung carcinoma A549 cells. Oncol Rep 5: 1137-1140.
34. Soda H, Raymond E, Sharma S, Lawrence R, Cerna C, et al. (1998) Antiproliferative effects of recombinant human bone morphogenetic protein-2 on human tumor colony-forming units. Anticancer Drugs 9: 327-331.
35. Beck S E, Jung B H, Del Rosario E, Gomez J, Carethers J M (2007) BMP-induced growth suppression in colon cancer cells is mediated by p21WAF1 stabilization and modulated by RAS/ERK. Cell Signal 19: 1465-1472.
36. Miyazaki H, Watabe T, Kitamura T, Miyazono K (2004) BMP signals inhibit proliferation and in vivo tumor growth of androgen-insensitive prostate carcinoma cells. Oncogene 23: 9326-9335.
37. Langenfeld E M, Kong Y, Langenfeld J (2006) Bone morphogenetic protein 2 stimulation of tumor growth involves the activation of Smad-1/5. Oncogene 25: 685-692.
38. Shepherd T G, Theriault B L, Nachtigal M W (2008) Autocrine BMP4 signalling regulates ID3 proto-oncogene expression in human ovarian cancer cells. Gene 414: 95-105. Epub 208 March 2004.
39. Gray M J, Dallas N A, Van Buren G, Xia L, Yang A D, et al. (2008) Therapeutic targeting of Id2 reduces growth of human colorectal carcinoma in the murine liver. Oncogene 27: 7192-7200. Epub 208 September 7122.
40. Chen S S, Claus R, Lucas D M, Yu L, Qian J, et al. Silencing of the inhibitor of DNA binding protein 4 (ID4) contributes to the pathogenesis of mouse and human CLL. Blood 117: 862-871. Epub 210 November 2022.
41. Noetzel E, Veeck J, Horn F, Hartmann A, Knuchel R, et al. (2008) [Promoter methylation of ID4. A marker for recurrence-free survival in human breast cancer]. Pathologe 29: 319-327.
42. Umetani N, Mori T, Koyanagi K, Shinozaki M, Kim J, et al. (2005) Aberrant hypermethylation of ID4 gene promoter region increases risk of lymph node metastasis in Ti breast cancer. Oncogene 24: 4721-4727.
43. Zou H, Wieser R, Massague J, Niswander L (1997) Distinct roles of type I bone morphogenetic protein receptors in the formation and differentiation of cartilage. Genes Dev 11: 2191-2203.
44. Korchynskyi 0, ten Dijke P (2002) Identification and functional characterization of distinct critically important bone morphogenetic protein-specific response elements in the Id1 promoter. J Biol Chem 277: 4883-4891.
45. Langenfeld E M, Kong Y, Langenfeld J (2005) Bone morphogenetic protein-2-induced transformation involves the activation of mammalian target of rapamycin. Mol Cancer Res 3: 679-684.
46. Yu P B, Hong C C, Sachidanandan C, Babitt J L, Deng D Y, et al. (2008) Dorsomorphin inhibits BMP signals required for embryogenesis and iron metabolism. Nat Chem Biol 4: 33-41. Epub 207 November 2018.
47. Hao J, Daleo M A, Murphy C K, Yu P B, Ho J N, et al. (2008) Dorsomorphin, a selective small molecule inhibitor of BMP signaling, promotes cardiomyogenesis in embryonic stem cells. PLoS One 3: e2904.
48. Yu P B, Deng D Y, Lai C S, Hong C C, Cuny G D, et al. (2008) BMP type I receptor inhibition reduces heterotopic [corrected] ossification. Nat Med 14: 1363-1369. Epub 208 November 1330.
49. U.S. patent application Ser. No. 12/537,037 filed Aug. 6, 2009.

What is claimed is:

1. A method of inhibiting cancer cell growth and/or promoting cancer cell death, comprising: administering to a cancer cell an effective amount of an antagonist of a type I BMP receptor, wherein the antagonist of a type I BMP receptor is a compound of the formula:

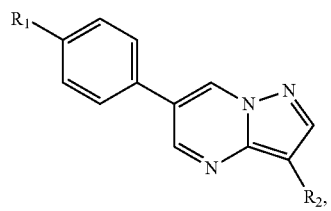

or pharmaceutically-acceptable salt thereof,
wherein $R_1$ is selected from the group consisting of alkyl, branched alkyl, substituted alkyl, aryl, substituted aryl, alkoxy, amino, and dialkylamino; and
wherein $R_2$ is selected from the group consisting of

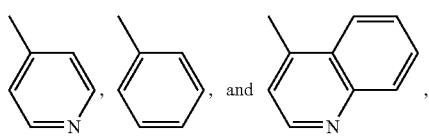

wherein the cancer cell is a lung cancer cell.

2. The method of claim 1, wherein $R_1$ is selected from the group consisting of

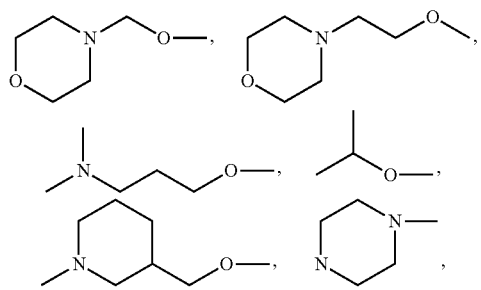

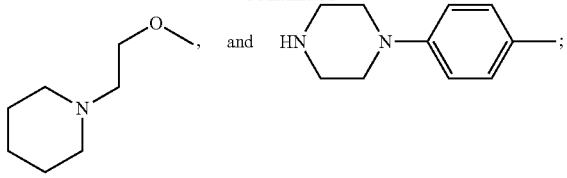

and
wherein $R_2$ is selected from the group consisting of

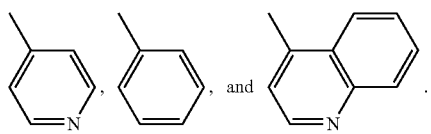

3. The method of claim 1, wherein the antagonist is a compound of the formula:

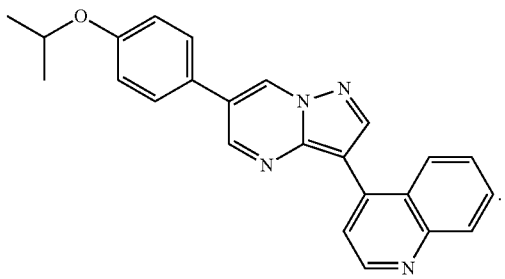 [SMILES: CC(C)Oc1ccc(-c2cnc3c(-c4ccnc5ccccc45)cnn3c2)cc1]

4. The method of claim 1, wherein the antagonist is a compound of the formula:

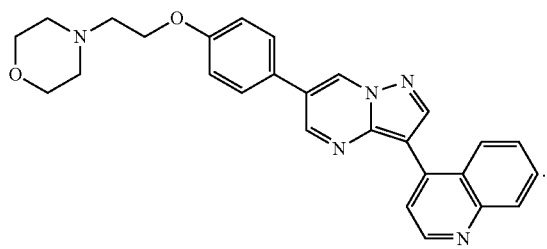 [SMILES: c1ccc2c(-c3cnn4cc(-c5ccc(OCCN6CCOCC6)cc5)cnc34)ccnc2c1]

5. The method of claim 1, wherein the antagonist is a compound of the formula:

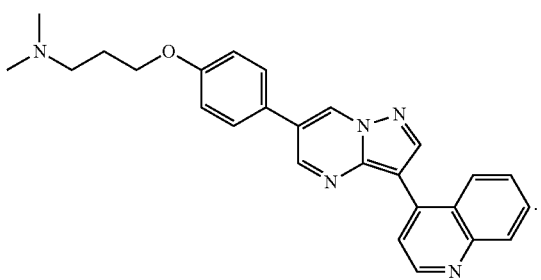

6. The method of claim 1, wherein the cancer cell is in a subject in need of treatment for a lung cancer, and the effective amount of the antagonist of a type I BMP receptor is administered to the subject for the treatment of the lung cancer.

7. The method of claim 6, and further comprising administering an anti-cancer agent and/or radiation to the subject.

8. A kit for inhibiting cancer cell growth and/or promoting cancer cell death, comprising: an antagonist of a type I BMP receptor; and a device for administering the BMP inhibitor, wherein the antagonist of a type I BMP receptor is a compound selected from the group consisting of

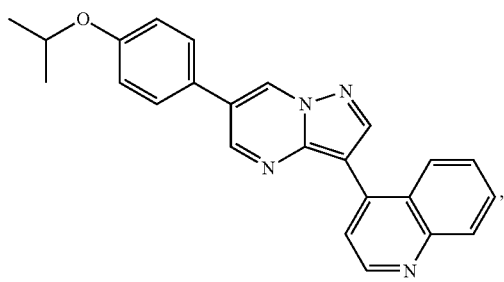

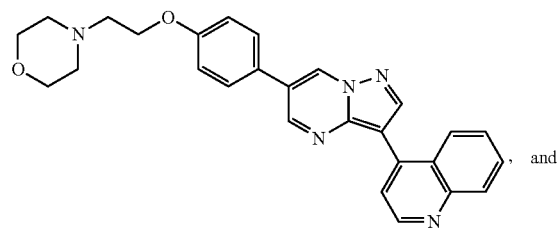, and

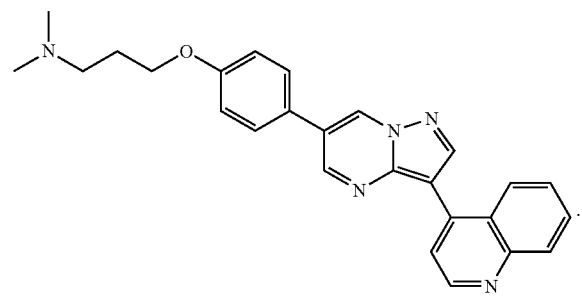 [SMILES: CN(C)CCCOc1ccc(-c2cnc3c(-c4ccnc5ccccc45)cnn3c2)cc1].

9. A method of inhibiting cancer cell growth and/or promoting cancer cell death, comprising: administering to a cancer cell an effective amount of an antagonist of a type I BMP receptor, wherein the antagonist of a type I BMP receptor is a compound selected from the group consisting of

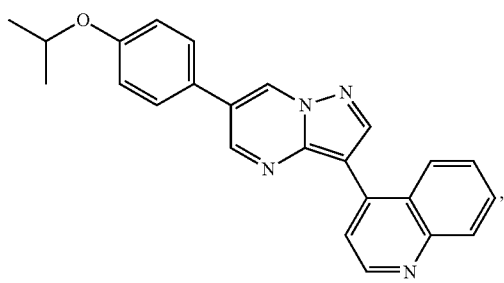

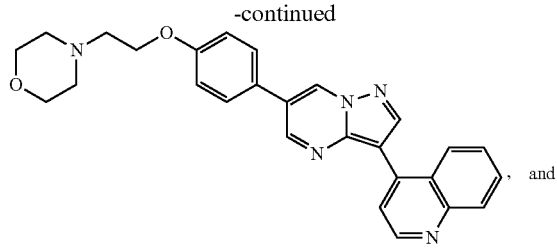, and

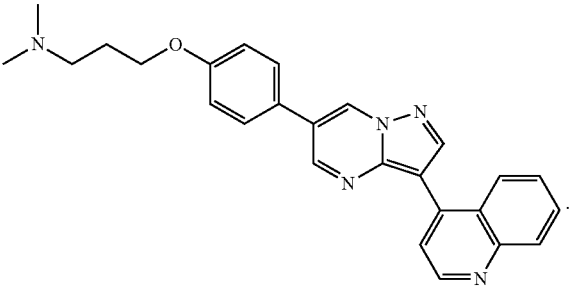.

10. The method of claim 9, wherein the antagonist is a compound of the formula:

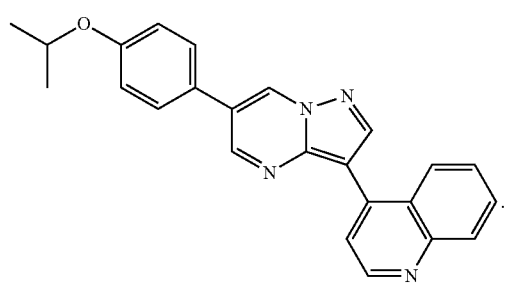 [SMILES: CC(C)Oc1ccc(-c2cnc3c(-c4ccnc5ccccc45)cnn3c2)cc1].

11. The method of claim 9, wherein the antagonist is a compound of the formula:

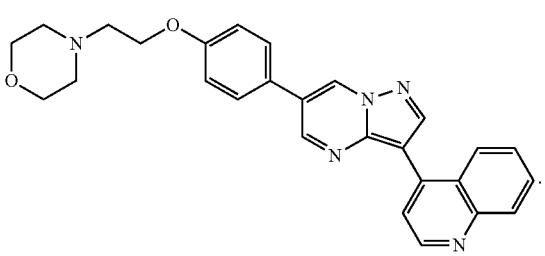 [SMILES: c1ccc2c(-c3cnn4cc(-c5ccc(OCCN6CCOCC6)cc5)cnc34)ccnc2c1].

12. The method of claim 9, wherein the antagonist is a compound of the formula:

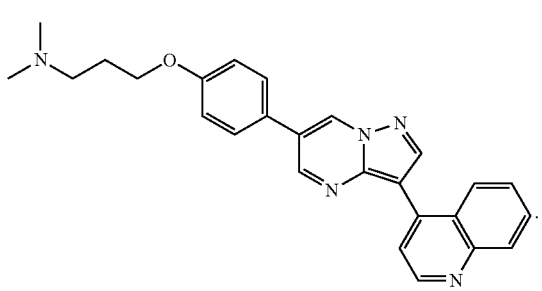 [SMILES: CN(C)CCCOc1ccc(-c2cnc3c(-c4ccnc5ccccc45)cnn3c2)cc1].

13. The method of claim 9, wherein the cancer cell is in a subject in need of treatment for a cancer, and the effective amount of the antagonist of a type I BMP receptor is administered to the subject for the treatment of the cancer.

14. The method of claim 13, and further comprising administering an anti-cancer agent and/or radiation to the subject.

* * * * *